United States Patent [19]

Hirayama et al.

[11] Patent Number: 5,795,891
[45] Date of Patent: Aug. 18, 1998

[54] ACYLPHENYLGLYCINE DERIVATIVE AND PREVENTIVE AND REMEDY FOR DISEASES CAUSED BY INCREASED COLLAGENASE ACTIVITY CONTAINING SAID COMPOUND AS ACTIVE INGREDIENT

[75] Inventors: Ryoichi Hirayama, Akashi; Takahiro Tsukida; Minoru Yamamoto, both of Osaka; Shoji Ikeda, Kobe; Fumio Sakamoto, Daito; Yuji Obata; Konomi Matsuo, both of Osaka, all of Japan

[73] Assignee: Kanebo Ltd., Tokyo, Japan

[21] Appl. No.: 596,278

[22] PCT Filed: Aug. 3, 1994

[86] PCT No.: PCT/JP94/01284

§ 371 Date: Feb. 8, 1996

§ 102(e) Date: Feb. 8, 1996

[87] PCT Pub. No.: WO95/04715

PCT Pub. Date: Feb. 16, 1995

[30] Foreign Application Priority Data

Aug. 9, 1993 [JP] Japan .................................. 5-218124

[51] Int. Cl.$^6$ .................................. C07C 259/06; A61K 31/16
[52] U.S. Cl. .................................. 514/238.2; 514/575; 544/175; 502/621
[58] Field of Search .................................. 514/238.2, 575; 562/621; 544/175

[56] References Cited

U.S. PATENT DOCUMENTS 5,387,610  2/1995  Gray et al. .................................. 514/575

*Primary Examiner*—Robert Gerstl
*Attorney, Agent, or Firm*—Millen, White, Zelano & Branigan, P.C.

[57] ABSTRACT

An acylphenylglycine derivative represented by general formula (I) or a pharmaceutically acceptable salt thereof, and a preventive and remedy for diseases caused by an increased collagenase activity containing the same as the active ingredient, wherein $R^1$ represents hydrogen atom, methyl, methylaminomethyl or morpholinomethyl; $R^2$ represents hydrogen atom, hydroxy, fluorine atom, or $C_1$–$C_4$ linear or branched alkyl; and $R^3$ represents $C_1$–$C_4$ linear or branched alkyl. The compound (I) and the salt maintains a potent collagenase inhibitor activity in the blood for long after being administered, and are useful as a remedy for various diseases believed to be caused by an increased collagenase activity.

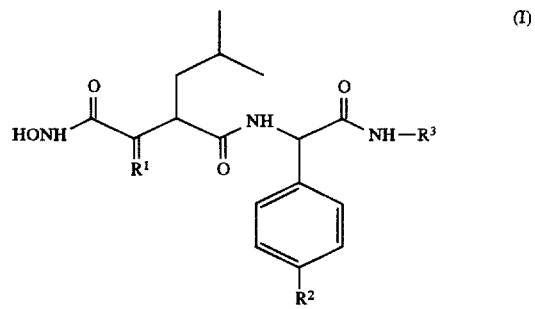

12 Claims, 1 Drawing Sheet

ACYLPHENYLGLYCINE DERIVATIVE AND PREVENTIVE AND REMEDY FOR DISEASES CAUSED BY INCREASED COLLAGENASE ACTIVITY CONTAINING SAID COMPOUND AS ACTIVE INGREDIENT

TECHNICAL FIELD

The present invention relates to novel acylphenylglycine derivatives or pharmaceutically acceptable salts thereof having collagenase inhibitory activity as well as to agents containing said derivatives as active ingredients for prophylaxis and treatment of diseases caused by increased collagenase activity. More specifically, the present invention relates to a novel acylphenylglycine derivative of the formula (I),

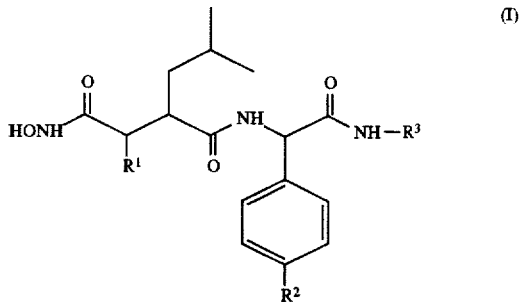

wherein $R^1$ represents a hydrogen atom, methyl, methylaminomethyl or morpholinomethyl; $R^2$ represents a hydrogen atom, hydroxy, fluorine atom, or $C_1$–$C_4$ linear or branched chain alkyl; and $R^3$ represents $C_1$–$C_4$ linear or branched alkyl, or a pharmaceutically acceptable salt thereof having collagenase inhibitory activity, and to an agent containing thereof as an active ingredient for prophylaxis and treatment of diseases caused by increased collagenase activity.

BACKGROUND ART

Collagenase is an enzyme involved in the metabolism of connective tissue matrix. Increased collagenase activity is considered to be a main cause of a variety of diseases including joint diseases, diseases due to bone resorption, periodontal diseases, corneal ulcer, epidermolysis bullosa and the like.

For example, in diseases of joint such as rheumatoid arthritis and osteoarthritis, increased collagenase activity has been reported by E. M. Gravallese et al. (Arthritis Rheum., 34(9): 1076 (1991)).

Diseases due to bone resorption is a class of diseases resulting from a remodeling process, which consists of formation and resorption of the bone, being biased in favor of resorption of the bone, and specific diseases such as hypercalcemia, osteoporosis are known to be included in this class. Attention has been attracted to the implication of cysteine proteases such as cathepsin L in the increased resorption of the bones in these diseases. However, a recent report by V. Everts et al. (J. Cell. Physiol., 150: 221 (1992)) indicates an additional implication of collagenase.

Thus, various compounds having collagenase inhibitory activity are investigated for they have a possibility to provide a remedy for those diseases with increased collagenase activity. See JP-A-62-103052 and JP-A-62-230757, JP-A-04-502008, and U.S. Pat. No. 5,114,953, for example. However, these compounds are not sufficient to maintain inhibitory activity in the blood after administration to a living body. Therefore, a need exists for a development of a compound which allows collagenase inhibitory activity to be maintained for a longer period of time at higher levels in the living body after administration.

SUMMARY OF THE INVENTION

The object of the present invention is to provide a novel compound with which collagenase inhibitory activity can be maintained for a long period at higher levels in the living body after administration and to provide an agent containing the compound as an active ingredient for prophylaxis and treatment of diseases caused by increased collagenase activity.

The inventors of the present invention found that an acylphenylglycine derivative of the formula (I),

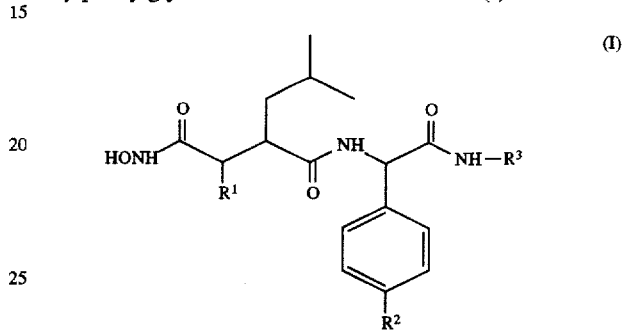

wherein $R^1$ represents a hydrogen atom, methyl, methylaminomethyl or morpholinomethyl; $R^2$ represents a hydrogen atom, hydroxy, fluorine atom, or $C_1$–$C_4$ linear or branched chain alkyl; and $R^3$ represents $C_1$–$C_4$ linear or branched chain alkyl, or pharmaceutically acceptable salt thereof meet the above requirements.

In this specification, the $C_1$–$C_4$ linear or branched chain alkyl group includes, for example, methyl, ethyl, n-propyl, isopropyl, n-butyl, sec-butyl or tert-butyl.

Among the compound of the present invention, an acylphenylglycine derivative in which $R^1$ and $R^3$ are both methyl and $R^2$ is hydrogen atom in the formula (I), or a pharmaceutically acceptable salt thereof has an excellent activity in a living body, thus being particularly preferred.

Stereoisomers exist due to the chiral carbon atoms ①, ② and ③ in the formula below when $R^1$ in the formula (I) is methyl, methylaminomethyl or morpholinomethyl, and stereoisomers due to the chiral carbon atoms ① and ② in the compound where $R^1$ is hydrogen atom.

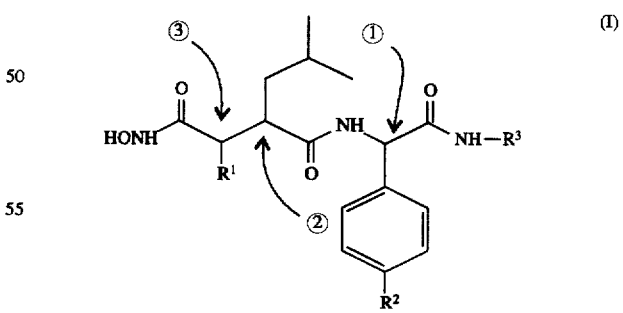

(wherein $R^1$, $R^2$ and $R^3$ are as defined above). The compound of the present invention include any of these stereoisomers and mixtures thereof. Of these stereoisomers, the compound having configurations (S) at the chiral carbon ① and (R) at the chiral carbon ② has a potent activity and thus particularly preferred.

Embodiments of the compound (I) of the present invention include, for example:

[4-(N-hydroxyamino)-2(R)-isobutylsuccinyl]-L-phenylglycine-N-methylamide

[4-(N-hydroxyamino)-2(R)-isobutylsuccinyl]-L-p-hydroxyphenylglycine-N-methylamide

[4-(N-hydroxyamino)-2(R)-isobutyl-3(R)-morpholinomethylsuccinyl]-L-phenylglycine-N-methylamide

[4-(N-hydroxyamino)-2(R)-isobutyl-3(S)-morpholinomethylsuccinyl]-L-phenylglycine-N-methylamide

[4-(N-hydroxyamino)-2(R)-isobutyl-3(R)-methylsuccinyl] L-phenylglycine-N-methylamide

[4-(N-hydroxyamino)-2(R)-isobutyl-3(S)-methylsuccinyl]-L-phenylglycine-N-methylamide

[4-(N-hydroxyamino)-2(R)-isobutyl-3(R)-methylaminomethylsuccinyl]-L-phenylglycine-N-methylamide

[4-(N-hydroxyamino)-2(R)-isobutyl-3(S)-methylaminomethylsuccinyl]-L-phenylglycine-N-methylamide

[4-(N-hydroxyamino)-2(R)-isobutylsuccinyl]-L-(p-isopropylphenyl)glycine-N-methylamide

[4-(N-hydroxyamino)-2(R)-isobutylsuccinyl]-L-phenylglycine-N-ethylamide.

Of these, [4-(N-hydroxyamino)-2(R)-isobutyl-3-methylsuccinyl]-L-phenylglycine-N-methylamide (the compound of Example 5) exhibits an excellent activity in the living body and therefore especially preferred.

Examples of the pharmaceutically acceptable salts of the compound (I) of the present invention include, for example, metallic salts such as sodium salt, potassium salt, calcium salt and the like. For the compound where $R^1$ is methylaminomethyl or morpholinomethyl, salts formed with inorganic acids such as hydrochloric acid and nitric acid, and salts formed with organic acids such as fumaric acid, maleic acid, methanesulfonic acid, are also included as examples.

The compound (I) and a pharmaceutically acceptable salt thereof can be produced by the method (A) below:

Method (A)

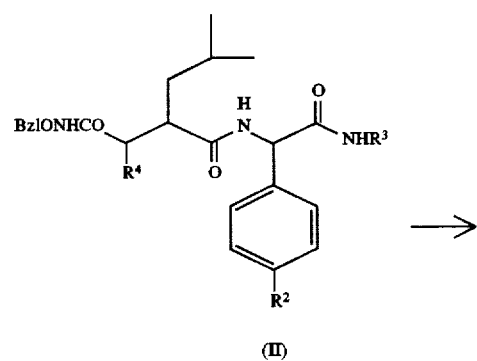

(II)

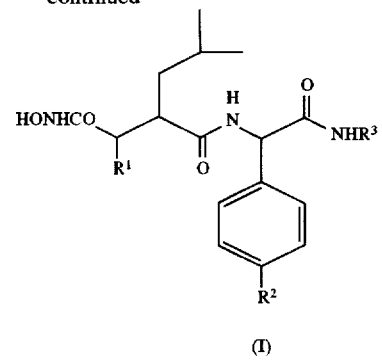

(I)

wherein Bzl represents benzyl, $R^4$ represents hydrogen atom, methyl, N-benzyl-N-methylaminomethyl or morpholinomethyl, and $R^1$, $R^2$ and $R^3$ are as defined above.

Thus, the compound (I) of the present invention or a pharmaceutically acceptable salt thereof can be produced by hydrogenolysis of the compound (II). The hydrogenolysis of the compound (II) may be usually carried out in a lower alcohol such as methanol or ethanol, which may, when required, contain water, hydrochloric acid, or N,N-dimethylformamide (abbreviated to DMF), in the presence of a catalyst such as 10% Pd/C and under a hydrogen atmosphere or pressurized hydrogen at room temperature to 60° C.

An optically active compound (I) may be produced by the hydrogenolysis of an optically active precursor compound (II). Alternatively, an optically active compound (I) may be produced by subjecting a diastereomeric mixture of compound (II) to hydrogenolysis to obtain compound (I) and performing separation by crystallization or one of chromatographical methods (high performance liquid chromatography (HPLC), preparative thin layer chromatography (P.TLC), etc.).

A compound (Ia) in which $R^1$ in the formula (I) is methyl may ba produced by the following method (B).

Method (B)

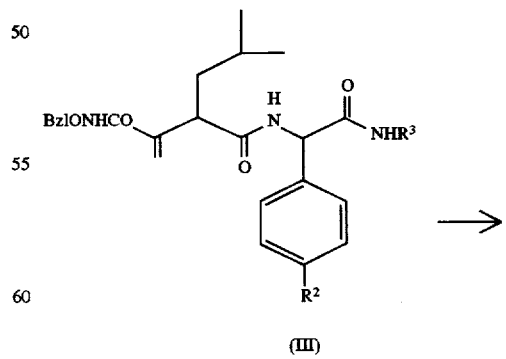

(III)

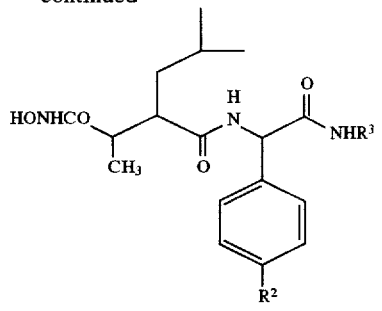

(Ia)

wherein Bzl, R² and R³ are as defined above.

Thus, the compound (Ia) may be obtained by catalytic reduction of the compound (III). For the catalytic reduction of the compound (III), analogous conditions may be employed to those shown for the method (A) above.

In the method (B), an optically active compound (Ia) may be obtained by subjecting an optically active precursor compound (III) to the reaction, and then by separation of the obtained diastereomeric mixture (Ia) by one of the above noted means.

The compound (I) of the present invention obtained by one of the methods (method A or B) may be converted to a pharmaceutically acceptable salt by a conventional method.

The preparation of the precursor compounds used in the methods (A) and (B) will be shown below.

Of the precursor compound (II) used in the method (A), a compound (IIa) in which R⁴ is hydrogen atom may be prepared by the following method:

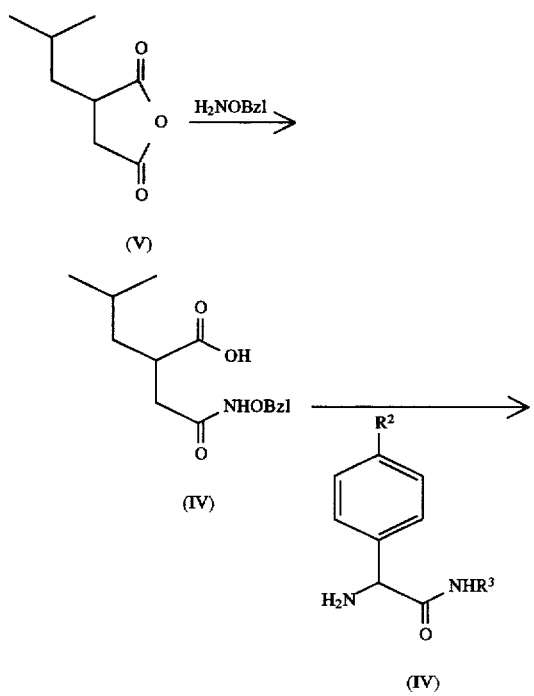

(V)

(IV)

(IV)

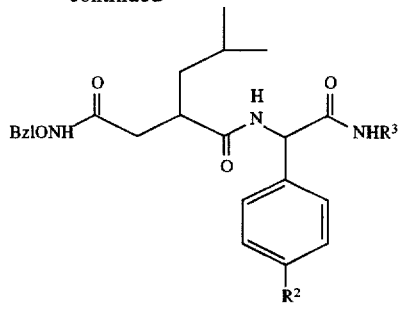

(IIa)

wherein Bzl, R² and R³ are as defined above.

Thus, a compound (VI) is first obtained by allowing to react a known anhydride (V) with an equivalent amount of o-benzylhydroxylamine in ether, tetrahydrofuran (hereinafter abbreviated to THF) or a mixed solvent thereof at −78° to 0° C. for 1 to 5 hours.

The compound (VI) and an amine (IV) are then subjected to condensation. The condensation reaction may be carried out using a condensation reagent commonly used in peptide synthesis (for example, dicyclohexylcarbodiimide (hereinafter abbreviated to DCC), 1-ethyl-3-(3-dimethylaminopropyl)carbodiimide hydrochloride (hereinafter abbreviated to WSC)) in an aprotic solvent such as DMF, THF or dichloromethane. The reaction is carried out generally at 0° C. to room room temperature for 2 to 24 hours. The molar ratio of compounds used in the reaction is: 0.8–1.5 mols for the compound (VI) and 1.0–1.5 mols for the condensation reagent, respectively, to 1 mol of the amine (IV).

The condensation reaction between the compound (VI) and the amine (IV) may be performed by the mixed acid anhydride method. In this case, the mixed acid anhydride is prepared by first dissolving the compound (VI) in an aprotic solvent noted above, adding to this an equivalent amount of tertiary amine such as triethylamine or N-methylmorpholine, and then by the addition, preferably, of a chlorocarbonic ester such as ethyl chloroformate or an acid chloride such as pivaloyl chloride at −20° to 5° C. The aimed compound (IIa) may be obtained by the addition of the amine (IV) and allowing the reaction at 0° C. to room temperature for 2 to 8 hours. For this reaction, 0.8–1.2 mols of the compound (VI) and 1.0–1.2 mols of chlorocarbonic ester or an acid chloride are generally used with respect to 1 mol of the amine (IV).

An optically active compound (IIa) may be obtained by the reaction between an optically active compound (VI) and an optically active amine (IV) which has been derived from a D- or L-phenylglycine. An optically active compound (VI) may be obtained by optical resolution of the compound (VI), which has been obtained as a racemic mixture by the aforementioned method, according to a conventional method utilizing an optically active amine, for example, cinchonidine or D-1-phenylethylamine, as a resolution agent.

Of the precursor compound (II) to be used in the method (A) above, a compound (IIb) in which R⁴ is methyl, N-benzyl-N-methylaminomethyl or morpholinomethyl may be produced by the following method:

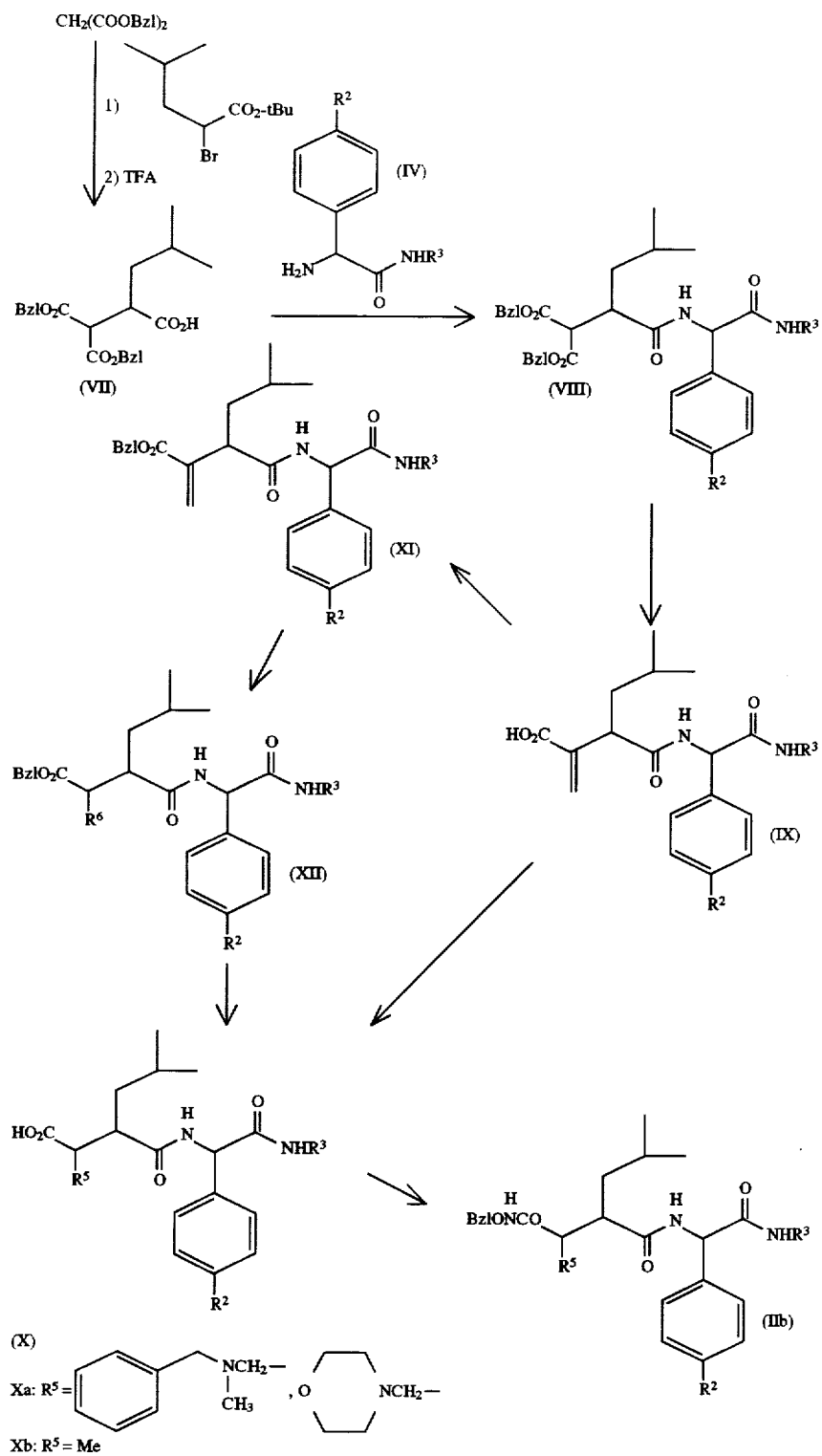

wherein $R^5$ represents methyl, N-benzyl-N-methylaminomethyl or morpholinomethyl, $R^6$ represents N-benzyl-N-methylaminomethyl or morpholinomethyl, TFA represents trifluoroacetic acid, and Bzl, $R^2$ and $R^3$ are as defined above.

Thus, dibenzyl malonate is first reacted with 2-bromo-4-methylpentanoic acid t-butyl ester (this may be prepared by reacting 2-bromo-4-methylpentanoic acid (known compound) with 2-methylpropene by a conventional method) in DMF in the presence of potassium t-butoxide, and the t-butyl ester derivative thus obtained is decomposed with trifluoroacetic acid to give the carboxylic acid derivative (VII).

Then, this carboxylic acid derivative (VII) is condensed with the amine (IV) by the method using a condensation reagent or by the mixed acid anhydride method noted above. The resulting dibenzyl ester (VIII) is then subjected to hydrogenolysis, and the dicarboxylic acid thus obtained is allowed to react with formaldehyde to give the α-methylenecarboxylic acid derivative (IX). For the hydrogenolysis of the dibenzyl ester (VIII), there are reaction conditions applicable in addition to one noted above for the hydrogenolysis of the compound (II), e.g., the reaction in which reduction is carried out in the presence of a reduction catalyst such as 10% Pd/C or Raney nickel and utilizing formic acid or ammonium formate as a hydrogen source. Preferably, the reaction between the dicarboxylic acid and formaldehyde is performed by mixing the dicarboxylic acid, an equimolar amount of base (e.g., piperidine) and a large excess, preferably 5 to 6 times molar amount, of formaldehyde aqueous solution and stirring overnight at room temperature, and then further refluxing by heat for 1 to 2 hours.

Then, the compound (IX) is reacted with N-benzylmethylamine or morpholine to give the compound Xa in which $R^5$ in the formula (X) is N-benzyl-N-methylaminomethyl or morpholinomethyl. Preferably the reaction is conducted by the use of an equimolar to 30 times molar amount of N-benzylmethylamine or morpholine and in a solvent such as THEF or free of solvent, at room temperature to 100° C. for several to 24 hours. Alternatively, the compound Xa may be obtained by converting the compound (IX) to its benzylester, compound (XI), converting this to the compound (XII) by the reaction with N-benzylmethylamine or morpholine, and then by hydrogenolysis of the compound (XII).

On the other hand, the compound Xb in which $R^5$ of the formula (X) is methyl may be obtained by catalytic reduction of the compound (IX). In this case, the same reaction conditions may be employed as aforementioned catalytic reduction in the method (B).

Finally, the compound (X) and O-benzylhydroxylamine are condensed by the aforementioned method utilizing a condensation reagent such as DCC or WSC or by the mixed acid anhydride method to thereby obtain the compound (IIb), i.e. the compound in which $R^4$ in the formula (II) is methyl, N-benzyl-N-methylaminomethyl or morpholinomethyl.

In order to obtain an optically active compound (IIb), an optically active compound (Ix) is first prepared using an optically active carboxylic acid (VII) and an optically active amine (IV). Then, reduction or the reaction with morpholine or N-benzylmethylamine gives the compound (X) as a diastereomeric mixture. The aimed configurational isomer is then isolated by means of crystallization, HPLC or the like, and reacted with O-benzylhydroxylamine to obtain the optically active compound (IIb). Alternatively, the optically active compound (IIb) may be obtained by condensation of the compound (X) as a diastereomeric mixture with O-benzylhydroxylamine, and isolating the optically active compound (IIb) from the thus obtained diastereomeric mixture of the compound (IIb) by the same method as mentioned above.

The precursor compound (III) used in the method (B) may be prepared from the above mentioned compound (IX) by the following method.

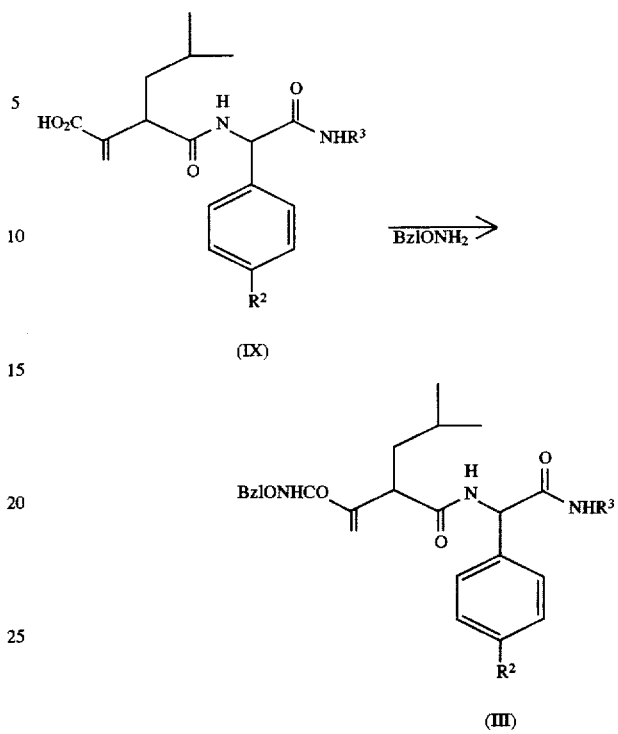

That is, as in the case of condensation of the compound (X) and O-benzylhydroxylamine, the compound (III) may be obtained by the condensation of the compound (IX) with O-benzylhydroxylamine using a condensation reagent or by the mixed acid anhydride method.

An optically active compound (III) may be readily obtained by the reaction of an optically active isomer of the compound (IX) with O-benzylhydroxylamine.

The compound (I) of the present invention or a pharmaceutically acceptable salt thereof may be administered to a human via an oral or parenteral route.

Examples of pharmaceutical preparation forms for oral administration include solid forms such as tablets, granules, powder, subtle granules, hard capsules and the like as well as liquid forms such as syrup and soft capsules.

These pharmaceutical preparations may be produced by conventional methods, i.e., tablets, granules, powder and fine granules may be produced by mixing the compound (I) of the present invention or a pharmaceutically acceptable salt thereof with conventional pharmaceutical additives such as lactose, starch, crystalline cellulose, magnesium stearate, hydroxypropylmethylcellulose, talc and the like; and hard capsules may be obtained by the encapsulation of aforementioned fine granules or powder.

A syrup may be produced by dissolving or suspending the compound (I) of the present invention or a pharmaceutically acceptable salt thereof in a solution containing sugar, carboxycellulose and the like. And soft capsules may be produced by dissolving or suspending the compound (I) of the present invention or a pharmaceutically acceptable salt thereof in a lipid vehicle such as vegetable oil, oily emulsion, glycols and the like, and filling this within soft capsule shells.

Examples of pharmaceutical preparation forms for parenteral administration include, in addition to injections, suppositories such as anal suppository and vaginal suppository, and for nasal application forms such as spray.

These pharmaceutical preparations may be produced by conventional methods. For example, injections may be produced by dissolving or emulsifying the compound (I) of the present invention or a pharmaceutically acceptable salt thereof in physiological saline or a lipid vehicle such as vegetable oil, oily emulsion, glycols arid the like, and aseptically enclosing the liquid within a ampule or vial.

The doses of the compound (I) of the present invention may differ according to the age, sex, body weight, symptoms and the like. In general, as the compound (I), the doses of 0.1 to 200 mg/kg body weight/day, preferably 1 to 100 mg/kg body weight/day will be proper and the daily doses will be administered at once or in 2 to 4 times of applications.

The compound of the present invention exhibit a potent collagenase inhibitory activity for an extended time period in the living body after administration and, additionally, have a good absorbability. This has been demonstrated in animal tests (see Test examples 1 and 2 below).

An investigation of its effect on arthritis was carried out in adjuvant arthritis model using erythrocyte sedimentation rate and swelling of the hind paw (increase in the volume of adjuvant-uninjected paw) as indexes, confirming that the compound of the present invention has an excellent effect (see Test Example 3 below). Also observed were suppressive effects on increases of urinary hydroxyproline excretion (ratio to creatinine) and in serum calcium concentration (See Test Example 3 below).

Furthermore, an investigation of its suppressive effect was carried out on bone resorption by administering the compound of the present invention to rats kept on a calcium-deficient food and using the urinary hydroxyproline excretion (ratio to creatinine) as an index. From this, it was found that the compound of the present invention lowered the amount of urine hydroxyproline (ratio to creatinine) (see Test Example 4 below).

On the other hand, the compound of the present invention exhibits only a low toxicity. For example, no death was observed after an oral administration of the compound of Example 5 to mice (3000 mg/kg body weight).

Therefore, the compound (I) of the present invention or a pharmaceutically acceptable salt thereof is useful as a prophylactic and therapeutic agent of diseases caused by elevated collagenase activity, e.g., diseases of joint such as rheumatoid arthritis and osteoarthritis and diseases due to bone resorption such as hypercalcemia and osteoporosis.

The action and effect of the present invention will be described in detail in Test Examples below.

EXAMPLES (Test Example 1)
Collagenase activity inhibition rate (in mice)
1. Tested compounds
Compound A . . . [4-(N-hydroxyamino)-2(R)-isobutylsuccinyl]-L-phenylglycine-N-methylamide (the compound of Example 1)
Compound B . . . [4-(N-hydroxyamino)-2(R)-isobutylsuccinyl]-L-(p-hydroxyphenyl)glycine-N-methylamide (the compound of Example 2)
Compound C . . . [4-(N-hydroxyamino)-2(R)-isobutyl-3-(morpholinomethyl)succinyl]-L-phenylglycine-N-methylamide hydrochloride (the compound of Example 4)
Compound D . . . [4-(N-hydroxyamino)-2(R)-isobutyl-3-methylsuccinyl]-L-phenylglycine-N-methylamide (the compound of Example 5)
Compound E . . . [4-(N-hydroxyamino)-2(R)-isobutyl-3-(methylaminomethyl)succinyl]-L-phenylglycine-N-methylamide (the compound of Example 6)
Compound F . . . [4-(N-hydroxyamino)-2(R)-isobutylsuccinyl]-L-phenylglycine-N-ethylamide (the compound of Example 7)
Compound G . . . [4-(N-hydroxyamino)-2(R)-isobutylsuccinyl]-L-(p-fluorophenyl)glycine-N-methylamide (the compound of Example 8)
Compound H . . . [4-(N-hydroxyamino)-2(R)-isobutylsuccinyl]-L-(p-isopropylphenyl)glycine-N-methylamide (the compound of Example 9)
Known compound X . . . [4-(N-hydroxyamino)-2(R)-isobutylsuccinyl]-L-O-methyltyrosine-N-methylamide (a compound described in JP-A-62-103052)
Known compound Y . . . [4-(N-hydroxyamino)-2(R)-isobutyl-3(S)-(2-thienyl)thiomethylsuccinyl]-L-phenylalanine-N-methylamide (a compound described in JP-A-4-502008)
Known compound Z . . . [4-(N-hydroxyamino)-2(R)-isobutylsuccinyl]-L-tryptophan-N-methylamide (a compound described in U.S. Pat. No. 5,114,953)

2. Test method

Test compounds were suspended in 0.5% CMC and orally administered to three mice per group (the dose of the test compound, 30 mg/kg), and after a certain period of time, the blood was collected in the presence of heparin and ice-cooled. Plasma was obtained by centrifugation of this blood at 10,000 rpm for 5 minutes at 4° C. To 400 μl of this plasma was added to 600 μl of distilled water, and heated at 100° C. for 10 minutes. After cooling, the mixture was centrifuged at 10,000 rpm for 5 minutes and filtered using a micro-volume ultrafiltration unit (Molcut II, Millipore) to provide a sample (A) for use in collagenase activity measurement. Using this sample, collagenase activity inhibition rate in blood was determined by the following method.

The sample (A) above was mixed with a known amount of collagenase (the collagenase used was prepared by the method described in JP-A-3-103178) dissolved in a buffer for measurement (50 mM Tris-HCl buffer, pH 7.5, containing 0.2M sodium chloride, 5 mM calcium chloride, 0.05% Brij-35 and 0.02% sodium azide.), and collagenase activity A was measured according to the method of Nagai et al. (Japanese Journal of Inflammation, 4, 123 (1984)) using a fluorescein isothiocyanate-labeled type-I collagen as a substrate. Simultaneously, sample (B) was prepared as described in the process for sample (A) using the blood collected from the mice which did not receive a test compound, and collagenase activity measurement was performed by the same method. Inhibition rate was determined from the following equation:

$$\text{Inhibition rate }(\%) = (1 - A/B) \times 100$$

3. Results

Table 1 shows the collagenase activity inhibition rates in blood at 1 and 3 hours following oral administration.

TABLE 1

| Collagenase Inhibition rates (%) in blood after oral administration | | |
|---|---|---|
| Tested compounds | After 1 hour | After 2 hours |
| Compound A | 88 | 83 |
| Compound B | 84 | 62 |
| Compound C | 75 | 64 |
| Compound D | 87 | 76 |
| Compound E | 82 | 61 |
| Compound F | 89 | 53 |
| Compound G | 83 | 64 |
| Compound H | 74 | 63 |
| Known compound X | 60 | 43 |
| Known compound Y | 14 | 21 |
| Known compound Z | 58 | 51 |

(Test Example 2)
Collagenase activity inhibition rate (in rats)
1. Tested compounds
Compound A . . . [4-(N-hydroxyamino)-2(R)-isobutylsuccinyl]-L-phenylglycine-N-methylamide (the compound of Example 1)
Known compound X . . . [4-(N-hydroxyamino)-2(R)-isobutylsuccinyl]-L-O-methyltyrosine-N-methylamide (a compound described in JP-A-62-103052)
2. Test method The same procedure as Test Example 1 was followed except that mice were replaced with rats (3 rats/group) and the dose of the tested compounds selected to be 100 mg/kg.
3. Test results Table 2 shows collagenase activity inhibition rates in the blood at 1, 3 and 6 hours following oral administration.

TABLE 2

| Tested compounds | Collagenase Inhibition rates (%) in blood after oral administration | | |
|---|---|---|---|
| | After 1 hr. | After 3 hrs. | After 6 hrs. |
| Compound A | 100 | 91 | 64 |
| Known compound X | 45 | 44 | 33 |

(Test Example 3)
Test by arthritis model
1. Tested compounds
Compound D . . . [4-(N-hydroxyamino)-2(R)-isobutyl-3-methylsuccinyl]-L-phenylglycine-N-methylamide (the compound of Example 5)
Known compound Y . . . [4-(N-hydroxyamino)-2(R)-isobutyl-3(S)-(2-thienyl)thiomethylsuccinyl]-L-phenylalanine-N-methylamide (a compound described in JP-A-4-502008)
2. Test method and evaluation items 8-week old male Lewis rats (Charles River Japan, K.K.) were divided into 4 groups (normal control group, control group, and two test compound groups) of 7 animals each. Each of the rats of the control group and the test compound groups were intra-dermally injected with 0.6 mg of heat-killed M. butyricum in 0.1 ml of liquid paraffin suspension in their right hind paw to induce adjuvant arthritis. The test compounds were suspended in 0.5% CMC, and administered to the rats of the test compound group at a dose of 100 mg/kg per administration immediately after the injection of adjuvant and at 12-hour intervals thereafter over a period of 20 days. The rats of the control group received 0.5% CMC immediately after the injection of adjuvant and at 12-hour intervals thereafter over a period of 20 days. The rats of the normal control group were not injected with adjuvant but only administered 0.5% CMC analogously to the administration of the test compounds.

Items of evaluation and methods for their measurement are as follows.

1) Hind paw volume

The volume of the hind paw was measured immediately before and on days 3, 7, 10, 14, 17 and 20 after the injection of adjuvant using a foot volume measuring apparatus. Analysis was made using t-test for superiority of the test compound group over the control group.

2) Erythrocyte sedimentation rates

The blood was fully removed on day 21 and used as a sample. Erythrocyte sedimentation measuring apparatus (Matsuyoshi's Erythrocyte Sedimentation rack) was used for the measurement, and statistical analysis was made according to the Dunnett's method for the superiority of the test compound group over the control group.

3) Blood calcium concentration

Measurement was carried out on the same sample as above 2) using Calcium Test$_{WAKO}$ (Wako Junyaku), and statistical analysis was made according to the Dunnett's method for the superiority of the test compound group over the control group.

4) Urine hydroxyproline

After the last administration of the test compounds on day 20, the rats were transferred into metabolic cages, and urine samples were collected overnight without supply of food or water. Urine volume and the amounts of creatinine and hydroxyproline were determined by the following method, and urinary hydroxyproline excretion expressed in the ratio to creatinine. Statistical analysis was made according to the Tukey's method for the superiority of test compound group over the control group. Determination of creatinine was carried out using Creatinine Test$_{WAKO}$ (Wako Junyaku). Hydroxyproline was determined by first hydrolyzing the urine with 6N hydrochloric acid, then isolation on high performance liquid chromatograph equipped with ion-exchange column (Hitachi Gel #2619), reaction with O-phthalaldehyde to form a hydroxyproline derivative, and measurement on a fluorophotometer.

4. Test results

1) Hind paw volume

FIG. 1 shows the time course of the volume change of adjuvant-uninjected hind paw. In the figure, lines n, c, y and d indicate the volume of the hind paw for the following groups, respectively:

n: normal group c: control group y: known compound Y-administered group d: compound D-administered group Statistical analysis was made using t-test for significant difference of the test compound group from the control group. The results are shown with * and **.

*P<0.05 *P<0.01

Compound D suppressed the swelling (volume increase) of the adjuvant-uninjected hind paw caused by the injection of adjuvant.

2) Erythrocyte sedimentation rates

Table 3 shows the erythrocyte sedimentation rates.

TABLE 3

| Groups | Erythrocyte sedimentation rates |
|---|---|
| Normal control group | 1 ± 0.1 |
| Control group | 33 ± 2 |
| Compound D group | 20 ± 2** |
| Compound Y group | 30 ± 3 |

**P < 0.01 (v.s. Control group)

While compound D significantly suppressed the increase in erythrocyte sedimentation rates caused by adjuvant injection, no such effect was noted for compound Y.

3) Serum calcium concentrations

Serum calcium concentrations are shown in Table 4.

TABLE 4

| Groups | Serum calcium conc. (mg/dl) |
| --- | --- |
| Normal control group | 8.6 ± 0.1 |
| Control group | 9.5 ± 0.1 |
| Compound D group | 8.9 ± 0.1** |
| Compound Y group | 9.6 ± 0.1 |

**P < 0.01 (v.s. Control group)

While compound D significantly suppressed the increase in serum calcium concentration, no such effect was noted for compound Y.

4) Urinary hydroxyproline excretion

Results from the measurement of urinary hydroxyproline excretion (ratio to creatinine) are shown in Table 5.

TABLE 5

| Groups | Urinary hydroxyproline excretion (μg/mg creatinine) |
| --- | --- |
| Normal control group | 71.8 ± 2.6 |
| Control group | 94.3 ± 1.8 |
| Compound D group | 78.4 ± 6.1 |
| Compound Y group | 107.1 ± 6.5 |

Compound D tended to suppress the increase in urinary hydroxyproline excretion.

(Test Example 4)
Test for inhibition of bone resorption
1. Tested compounds
Compound D . . . [4-(N-hydroxyamino)-2(R)-isobutyl-3-methylsuccinyl]-L-phenylglycine-N-methylamide (the compound of Example 5)
Known compound Y . . . [4-(N-hydroxyamino)-2(R)-isobutyl-3(S)-(2-thienyl)thiomethylsuccinyl]-L-phenylalanine-N-methylamide (a compound described in JP-A-4-502008)
2. Test method 6-week old male Wister rats (SLC Japan) were kept on a calcium-deficient food (Oriental Yeast, 0.0105–0.012% calcium, 0.62% phosphorus), orally administered 100 mg/kg of compound D or Y in a 0.5% CMC suspension on day 6 and, immediately thereafter, urine was collected for 16 hours under the condition of fasting with free access to water. The urine volume and urinary hydroxyproline and creatinirie content were measured by the method described in Example 3, and the urine hydroxyproline/creatinie ratio was calculated. Statistical analysis was made using the Tukey's method for the superiority of the test compound group over the control group.
4. Test results Urine hydroxyproline/creatinine ratio is shown in Table 6.

TABLE 6

| Groups | Urinary hydroxyproline excretion (μg/mg creatinine) |
| --- | --- |
| Normal control group | 134 ± 7 |
| Control group | 174 ± 7 |
| Compound D group | 144 ± 5* |
| Compound Y group | 161 ± 3 |

* P < 0.05 (v.s. Control group)

Compared with the normal control group, urine hydroxyproline/creatinine ratio significantly increased in the control group. While the compound Y hardly suppressed this increase, the compound D exhibited a significant suppression from the level of the control group.

THE BEST MODE OF CARRYING OUT THE INVENTION

Figure 1:
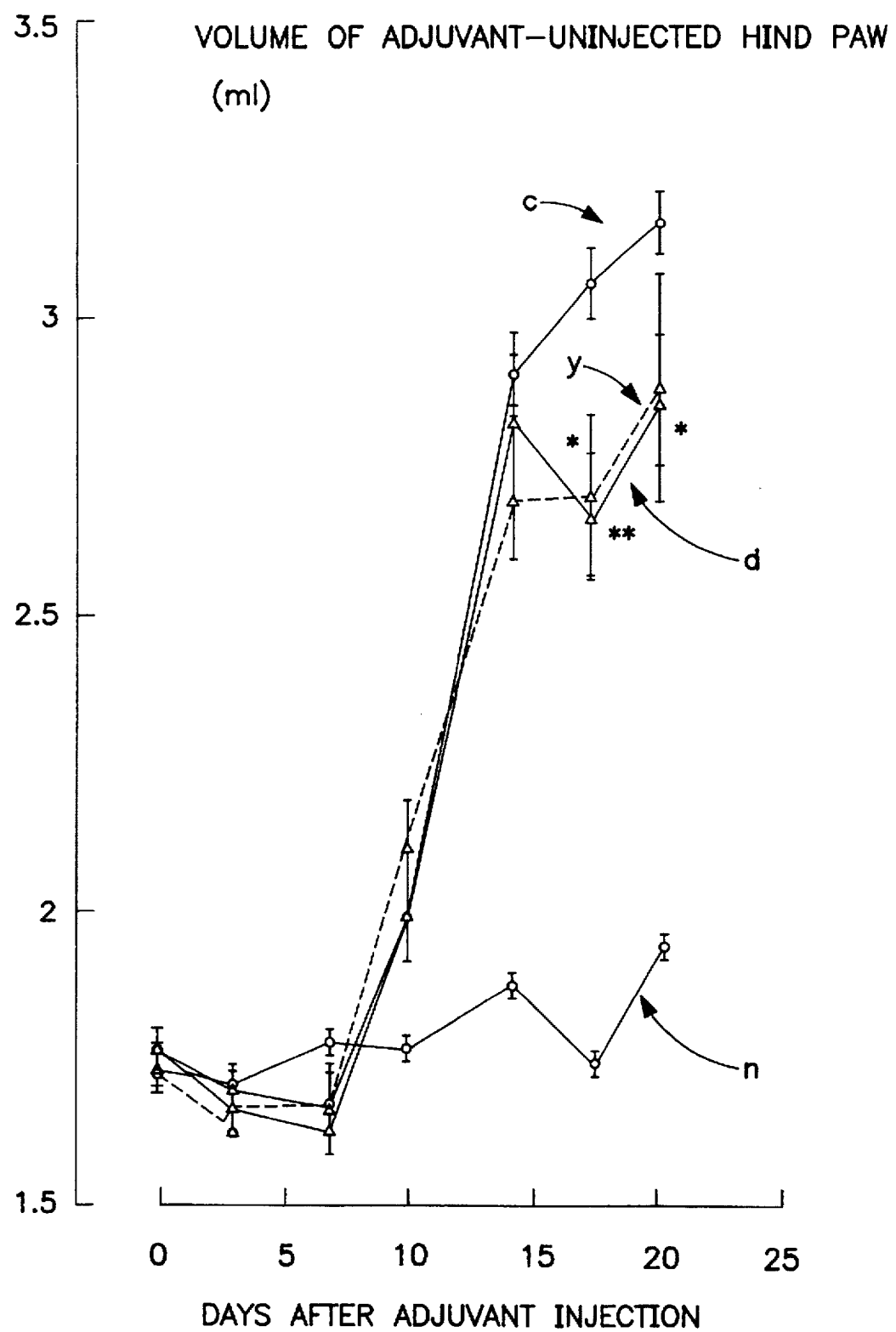
FIG. 1 shows the time profile of the volume of the adjuvant-uninjected hind paw in the test on prophylaxis of adjuvant arthritis (Test Example 3).

The present invention will be explained in further detail with reference to Reference examples and Examples.

Reference Example 1

Preparation of [4-(N-benzyloxyamino)-2(R)-isobutylsuccinyl]-L-phenylglycine-N-methylamide
[an optically active isomer in which $R^2$ is hydrogen atom and $R^3$ is methyl in the formula (IIa)]
(1) 4-(N-benzyloxyamino)-2(R)-isobutylsuccinic acid 124 g of dihydro-3-(RS)-(2-methylpropyl)-2,5-furandione was dissolved in 400 ml of ether and to this solution was added dropwise, at 0° C., 400 ml of an ether solution of 128 g of O-benzylhydroxylamine hydrochloride neutralized with potassium carbonate. After stirring for 3.5 hours, resulting white solid was collected by filtration. Washing with 300 ml of a mixed solvent of ether and ethyl acetate (ether/ethyl acetate=2/1) gave 98.6 g of 4-(N-benzyloxyamino)-2(RS)-isobutylsuccinic acid.

Then, the obtained 98.6 g of 4-(N-benzyloxyamino)-2(RS)-isobutylsuccinic acid was dissolved in 2000 ml of DMF, and after the addition of 42.8 g of D-1-phenylethylamine dissolved in 1000 ml of DMF, the mixture was allowed to stand overnight at room temperature. The resulting crystals were recrystallized from 2000 ml of DMF. To the crystals thus obtained was added 600 ml of 2N hydrochloric acid, the mixture extracted with 500 ml of ethyl acetate, washed with water and dried over magnesium sulfate. Evaporation of the solvent in vacuo gave 30.5 g of 4-(N-benzyloxyamino)-2(R)-isobutylsuccinic acid.

Melting point: 93°–95° C.
$[\alpha]_D$=+21° (C=0.5, MeOH)
$^1$H-NMR (DMSO-$d_6$) δ: 0.85 (6H,t), 1.12–1.22 (1H,m), 1.37–1.60 (2H,m), 2.05 (1H,dd), 2.24 (1H,dd), 2.64–2.73 (1H,m), 4.76 (2H,s), 7.38 (5H,s), 11.0 (1H,s), 12.2 (1H,s).

(2) N-benzyloxycarbonyl-L-phenylglycine-N-methylamide 35.2 g of N-benzyloxycarbonyl-L-phenylglycine and 14.9 g of triethylamine were dissolved in 900 ml of THF. To this was added dropwise 16.0 g of ethyl chloroformate under ice-cooling and the mixture stirred for about 30 minutes at 5°–6° C. to prepare a mixed acid anhydride, and this was followed by an addition of 28.7 g of 40% methylamine methanol solution and stirring for 2 hours under ice-cooling. After filtering off of insoluble matter, ethyl acetate was added to the solution and the mixture washed with 1N hydrochloric acid, saturated sodium bicarbonate aqueous solution and then with water, successively. The ethyl acetate layer was dried over anhydrous magnesium sulfate and the solvent evaporated in vacuo, washing of the residue with a mixed solvent of n-hexane and ether gave 33.3 g of N-benzyloxycarbonyl-L-phenylglycine-N-methylamide (yield: 90.7%).

$^1$H-NMR (DMSO-$d_6$) δ: 2.55 (3H,d), 4.98 (2H,s), 5.16 (1H,d), 7.2–7.5 (10H,m), 7.6–7.4 (1H,m), 7.95–8.2 (1H,d).

(3) [4-(N-benzyloxyamino)-2(R)-isobutylsuccinyl]-L-phenylglycine-N-methylamide

To 27 g of N-benzyloxycarbonyl-L-phenylglycine-N-methylamide dissolved in 400 ml of methanol was added 500 mg of 10% Pd/C and catalytic reduction conducted under a hydrogen atmosphere at 3–4 kg/cm². The removal of the catalyst by filtration and concentration in vacuo gave L-phenylglycine-N-methylamide as an oil. This oil was dissolved in 400 ml of DMF and to this were added 24.4 g of 4-(N-benzyloxyamino)-2(R)-isobutylsuccinic acid and 17.8 g of WSC and the mixture was stirred overnight at room temperature. After concentration in vacuo, the residue obtained was dissolved in 1 l of chloroform and the solution washed with 0.1N hydrochloric acid, saturated sodium bicarbonate aqueous solution and water, successively, and dried over anhydrous sodium sulfate. After evaporation of chloroform, the solid thus obtained was recrystallized from a mixed solvent of ethyl acetate/methanol, yielding 29 g of colorless crystals (yield: 73%).

Melting point: 230°–232° C.

$^1$H-NMR (DMSO-$d_6$) δ: 0.82 (3H,d,J=6.3 Hz), 0.87 (3H, d, J=6.3 Hz), 1.0–1.1 (1H,m), 1.35–1.55 (2H,m), 1.97 (1H, dd,J=7, 14.4 Hz), 2.13 (1H, dd,J=7.4, 14.4 Hz), 2.57 (3H, d, J=4.5 Hz), 2.8–2.95 (1H, m), 4.66 (1H, d, J=11 Hz), 4.71 (1H, d, J=11 Hz), 5.38 (1H, d, J=7.8 Hz), 7.2–7.4 (5H, m), 8.13 (1H, q, J=4.5 Hz), 8.45 (1H, d, J=7.8 Hz), 10.9 (1H, s).

IR (KBr)cm$^{-1}$: 3292, 3224, 2960, 1660, 1646, 1566, 1538.

Elementary analysis (for $C_{24}H_{31}N_3O_4$) Calcd. (%) C, 67.74; H, 7.34; N, 9.87 Found (%) C, 67.49; H, 7.25; N, 9.73

Reference Example 2

Preparation of [4-(N-benzyloxyamino)-2(R)-isobutylsuccinyl]-L-(p-hydroxyphenyl)glycine-N-methylamide [an optically active isomer in which $R^2$ is hydroxy and $R^3$ is methyl in the formula (IIa)]

1.3 g of 4-(N-benzyloxyamino)-2(R)-isobutylsuccinic acid and 0.7 g of L-(p-hydroxyphenyl)glycine-N-methylamide (prepared by the method described in JP-A-54-84546) were dissolved in 20 ml of DMF. To this was added dropwise 0.54 g of WSC under ice-cooling with stirring and the mixture was stirred overnight at room temperature. After concentration in vacuo, to the residue obtained were added 15 ml of chloroform and 15 ml of 0.1N hydrochloric acid and the mixture was stirred. The precipitating solid was collected by filtration and recrystallized from a THF-hexane mixed solvent, yielding 0.54 g of colorless crystals (yield: 24.8%).

$^1$H-NMR(DMSO-$d_6$) δ: 0.81 (3H,d,J=6.3 Hz), 0.86 (3H, d, J=6.3 Hz), 1.0–1.1 (1H, m), 1.35–1.55 (2H, m), 1.96 (1H, dd, J=7, 14.5 Hz), 2.12 (1H, dd, J=7.3, 14.5 Hz), 2.56 (3H, d, J=4.5 Hz), 2.6–2.7 (1H, m ), 4.68 (1H, d,J=10.9 Hz), 4.72 (1H, d, J=10.9 Hz), 5.25 (1H, d, J=7.7 Hz), 6.67 (2H, d, J=8.5 Hz), 7.16 (2H, d, J=8.5 Hz), 7.36 (5H, s), 7.97 (1H, q, J=4.5 Hz), 8.28 (1H, d, J=7.8 Hz), 9.34 (1H, s), 10.96 (1H,s)

Reference Example 3

Preparation of [4-(N-benzyloxyamino)-2(R)-isobutyl-3-(morpholinomethyl)succinyl]-L-phenylglycine-N-methylamide [an optically active isomer (diastereomer "a'") in which $R^2$ is hydrogen atom, $R^3$ is methyl and $R^5$ is morpholinomethyl in the formula (IIb)]

(1) 2(R)-bromo-4-methylpentanoic acid t-butyl ester 33 g of 2(R)-bromo-4-methylpentanoic acid (prepared from D-leucine) was dissolved in 100 ml of methylene chloride. To this solution, at −40° C. was introduced 47 g of 2-methylpropene while stirring, and after the addition of 0.8 ml of sulfuric acid the mixture was stirred overnight at room temperature. The reaction mixture was concentrated to ½ in vacuo and washed with 10% sodium carbonate aqueous solution and dried over anhydrous magnesium sulfate. The solution was then evaporated in vacuo, yielding 37.4 g of 2(R)-bromo-4-methylpentanoic acid t-butyl ester.

$[α]_D$=+29° (c=2, MeOH)

1H-NMR (CDCl$_3$) δ: 0.92 (3H, d), 0.95 (3H, d), 1.45 (9H, s), 1.7–2.0 (3H, m), 4.18 (1H, t)

(2) 2-benzyloxycarbonyl-3(R)-hydroxycarbonyl-5-methylhexanoic acid benzyl ester

To 68 g of dibenzyl malonate dissolved in 500 ml of DMF was gradually added 26.5 g of potassium t-butoxide under ice-cooling while stirring. To this was then added dropwise, over 1 hour at 0° C., 54.5 g of 2(R)-bromo-4-methylpentanoic acid t-butyl ester dissolved in 100 ml of DMF and the mixture stirred at 0°–5° C. for 4 days. To the reaction mixture were added 500 ml of ethyl acetate and 300 ml of saturated ammonium chloride aqueous solution and the mixture was stirred well. The organic layer was then separated and the aqueous layer was extracted with 500 ml of ethyl acetate. The combined organic layer was washed with a NaCl aqueous solution, dried over anhydrous magnesium sulfate and concentrated in vacuo, yielding an oil. This was subjected to isolation and purification using silica gel medium-pressure liquid chromatography (n-hexane/ethyl acetate=30/1) to yield 48.9 g of 2-benzyloxy-3(R)-t-butoxycarbonyl-5-methylhexanoic acid benzyl ester.

Then, 23.2 g of this 2-benzyloxycarbonyl-3(R)-t-butoxycarbonyl-5-methylhexanoic acid benzyl ester was dissolved in 75 ml of 95% trifluoroacetic acid aqueous solution and stirred overnight at room temperature. Trifluoroacetic acid was evaporated off in vacuo, the residue dissolved in 100 of methylene chloride, washed with saturated NaCl aqueous solution and dried over anhydrous magnesium sulfate. After concentration in vacuo, syrup thus obtained was dissolved in 70 ml of ether and, after addition of 200 ml of n-hexane, precipitated crystals were removed by filtration and the filtrate was concentrated in vacuo, yielding 12.5 g of 2-benzyloxy-3(R)-hydroxycarbonyl-5-methylhexanoic acid benzyl ester.

$[α]_D$=+30° (c=2, MeOH)

1H-NMR (DMSO-$d_6$) δ: 0.77 (6H, d, J=6.4 Hz), 1.0–1.1 (1H, m), 1.4–1.6 (2H, m), 2.8–3.0 (1H, m), 3.71 (1H, d,J=10 Hz), 5.09–5.25 (2H, m), 7.2–7.4 (10H, m)

(3) [4-benzyloxy-3-benzyloxycarbonyl-2(R)-isobutylsuccinyl]-L-phenylglycine-N-methylamide [an optically active isomer in which $R^2$ is hydrogen atom and $R^3$ is methyl in the formula (VIII)]:

23 g of 4-benzyloxy-3-benzyloxycarbonyl-2(R)-isobutylsuccinic acid and 10.3 g of L-phenylglycine-N-methylamide were dissolved in 100 ml of DMF. To this solution were added, under ice-cooling, 10.6 g of N-hydroxybenzotriazol, 3.6 g of 4-dimethylaminopyridine and 13.3 g of WSC and the mixture was stirred overnight at room temperature. The reaction mixture was concentrated in vacuo and the residue dissolved in 800 ml of ethyl acetate and washed with water, 0.1% hydrochloric acid, saturated sodium bicarbonate aqueous solution and saturated sodium chloride aqueous solution, dried over anhydrous magnesium sulfate and concentrated in vacuo, yielding [4-benzyloxy-3-benzyloxycarbonyl-2(R)-isobutylsuccinyl]-L-phenylglycine-N-methylamide as colorless crystals (26.6 g, yield; 95%).

$^1$H-NMR (DMSO-$d_6$) δ: 0.75 (3H, d, J=6.5 Hz), 0.82 (3H, d, J=6.4 Hz), 1.0–1.1 (1H, m), 1.4–1.6 (2H, m), 2.56 (3H, d, J=4.6 Hz), 3.2–3.35 (1H, m), 3.67 (1H, d, J=10 Hz), 4.95 (2H, s), 5.07 (1H, d, J=12.4 Hz), 5.16 (1H, d, J=12.4 Hz), 5.39 (1H, d, J=7.7 Hz), 7.15–7.45 (15H, m), 8.11 (1H, q, J=4.6 Hz), 8.74 (1H, d, J=7.7 Hz)

(4) [4-hydroxy-2(R)-isobutyl-3-methylenesuccinyl]-L-phenylglycine-N-methylamide [an optically active isomer in which $R^2$ is hydrogen atom and $R^3$ is methyl in the formula (IX)]

26 g of the compound obtained in (3) above was dissolved in 600 ml of ethanol. To this solution were added 20 g of ammonium formate and 6 g of 10% Pd/C and the mixture was stirred for 1.5 hours at room temperature. After removal of the Pd/C by filtration, 5.2 g of piperidine was added to the filtrate and the mixture stirred for 30 minutes. Then, following addition of 32.7 ml of formaldehyde aqueous solution (37%) and stirring for 18 hours at room temperature, the mixture was heat refluxed for 1.5 hours. After concentration in vacuo, the residue thus obtained was dissolved in 500 ml of 10% sodium citrate aqueous solution and extracted with ethyl acetate (500 ml×5 times). The organic layer then was extracted with 10% potassium carbonate aqueous solution (300 ml×3 times), the extract adjusted to pH 4 wit dilute hydrochloric acid and extracted with methylene chloride (400 ml×5 times).

The combined extract was dried over anhydrous magnesium sulfate and concentrated in vacuo, yielding [4-hydroxy-2(R)-isobutyl-3-methylenesuccinyl]-L-phenylglycine-N-methylamide as colorless crystalline powder (12.3 g, yield; 69%).

$^1$H-NMR (DMSO-d$_6$) δ: 0.83 (3H, d, J=6.4 Hz), 0.88 (3H, d, J=6.4 Hz), 1.3–1.7 (1H, m), 1.4–1.6 (2H, m), 2.57 (3H, d, J=4.6 Hz), 3.6–3.7 (1H, m), 5.37 (1H, d, J=7.8 Hz), 5.6 (1H, s), 6.1 (1H, s), 7.2–7.4 (5H, m), 8.16 (1H, q, J=4.6 Hz), 8.33 (1H, d, J=7.8 Hz), 12.6 (1H, bs).

(5) [4-hydroxy-2(R)-isobutyl-3(RS)-(morpholinomethyl)succinyl]-L-phenylglycine-N-methylamide [a diastereomeric mixture of the compound in which $R^2$ is hydrogen atom, $R^3$ is methyl and $R^5$ is morpholinomethyl]

To 12 g of the crystals obtained in (4) above was added 100 ml of morpholine and the mixture stirred for 2 day at 40°–45° C. Following concentration in vacuo, the residue obtained was dissolved in 300 ml of 5% sodium bicarbonate aqueous solution and washed with ether. The aqueous layer was adjusted to pH 1 with dilute hydrochloric acid, concentrated in vacuo until solvent amount was reduced to ⅕–⅙, and extracted with chloroform (300 ml×5 times). The extract was dried over anhydrous magnesium sulfate and concentrated in vacuo, yielding 11.6 g of [4-hydroxy-2(R)-isobutyl-3(RS)-(morpholinomethyl)succinyl]-L-phenylglycine-N-methylamide hydrochloride (mixture of two diastereomers derived from the chiral carbon atom at position 3) (yield; 70%).

A minute amount of this diastereomeric mixture was separated for analytic purpose by HPLC under the following conditions:

HPLC conditions: column: Inertsil ODS-2 (4.6×150 mm), GL Science,

Mobile phase: 0.1% TFA aqueous/acetonitril=7:3

Flow rate: 1 ml/min

NMR for one of the diastereomers exhibited the following spectrum.

$^1$H-NMR (DMSO-d$_6$) δ: 0.84 (3H, d, J=6.5 Hz), 0.90(3H, d,J=6.4 Hz), 1.1–1.2 (1H, m), 1.45–1.65 (2H, m), 2.57 (3H, d, J=4.6 Hz), 2.9–3.15 (7H,m), 3.16–3.9 (5H, m), 5.38 (1H, d, J=7.4 Hz), 7.2–7.5 (5H, m), 8.6 (1H, q, J=4.6 Hz), 8.81 (1H, d, J=7.6 Hz).

(6) [4-(N-benzyloxyamino)-2(R)-isobutyl-3-(morpholinomethyl)succinyl]-L-phenylglycine-N-methylamide [an optically active isomer in which $R^2$ is hydrogen atom, $R^3$ is methyl and $R^5$ is morpholinomethyl in the formula (IIb) (diastereomer "a'")]

Then, 2.65 g of the diastereomeric mixture in (5) above and 1.08 g of O-benzylhydroxylamine hydrochloride and 1 g of hydroxybenzotriazol were dissolved in a mixed solvent of 50 ml methylene chloride/25 ml DMF, to this was added, under ice-cooling, 1.29 g of WSC and then 1.2 ml of N-methylmorpholine and the mixture stirred overnight at room temperature. The reaction mixture was concentrated in vacuo, the residue thus obtained dissolved in chloroform, washed with water and then saturated sodium bicarbonate aqueous solution, and dried over anhydrous magnesium sulfate. Concentration in vacuo gave solid, which was a mixture of two stereoisomers (referred to as diastereomer "a'" and "b+", respectively) which were eluted with a retention time of 5.9 minutes and 6.6 minutes, respectively, in the following HPLC analysis.

HPLC conditions: column: Inertsil ODS-2 (4.6×150 mm), GL Science,

Mobile phase: 0.1% TFA aqueous/acetonitril=7.3

Flow rate: 1 ml/min (ratio of peak areas for diastereomers "a'" and "b'" being about 5:1)

The mixture of diastereomers "a'" and "b'" was dissolved in methanol, and crystallization performed by ether addition, giving 1.56 g of an optically active isomer of [4-(N-benzyloxyamino)-2(R)-isobutyl-3-(morpholinomethyl)succinyl]-L-phenylglycine-N-methylamide (diastereomer "a'") (yield; 51%).

$^1$H-NMR (DMSO-d$_6$) δ: 0.77 (3H, d, J=6.4 Hz), 0.82 (3H, d, J=6.4 Hz), 0.85–0.9 (1H,m), 1.35–1.45 (2H, m), 1.73 (1H, dd, J=3.1, 11.8 Hz), 1.9–2.0 (2H, m), 2.55–2.7 (2H, m), 2.57 (3H, d, J=4.6 Hz), 3.3–3.5 (4H, m), 4.76 (1H, d, J=11.3 Hz), 4.81 (1H, d, J=11.3 Hz), 5.45 (1H, d, J=8 Hz), 7.2–7.45 (10H, m), 8.1 (1H, q, J=4.6 Hz), 8.71 (1H, d, J=8 Hz), 11.0(1H,s).

Reference Example 4

[4-(N-benzyloxyamino)-2(R)-isobutyl-3-methylenesuccinyl]-L-phenylgnycine-N-methylamide [an optically active isomer in which $R^2$ is hydrogen atom and $R^3$ is methyl in the formula (III)]

0.3 g of [4-hydroxy-2(R)-isobutyl-3-methylenesuccinyl]-L-phenylglycine-N-methylamide obtained in Reference example 3 (4) and 0.1 g of triethylamine were dissolved in 20 ml of THF, and to the solution was added, under ice-cooling while stirring, 0.108 g of ethyl chloroformate and the mixture stirred for 10 minutes. To the mixture then were added 0.144 g of O-benzylhydroxylamine hydrochloride and 0.1 g of triethylamine, and the mixture was stirred for 1 hour at room temperature. After removal of insoluble matter by filtration, the filtrate was washed with 1N hydrochloric acid and then with water, dried over anhydrous magnesium sulfate, and concentrated in vacuo. Purification of the thus obtained residue by preparative TLC gave 135 mg of [4-(N-benzyloxyamino)-2(R)-isobutyl-3-methylenesuccinyl]-L-phenylglycine-N-methylamide (34.3%).

$^1$H-NMR (DMSO-d$_6$) δ: 0.81 (3H, d, J=6.4 Hz), 0.86 (3H, d, J=6.4 Hz), 1.25–1.65 (3H, m), 2.56 (3H, d, J=4.5 Hz), 3.58 (1H, t, J=7 Hz), 4.79 (2H, s), 5.36 (1H, d, J=7.9 Hz), 5.37 (1H, s), 5.58 (1H, s), 7.2–7.45 (10H, m), 8.21 (1H, q, J=4.5 Hz), 8.48 (1H, d, J=7.8 Hz), 11.4 (1H, s).

(5) Reference Example 5

[4-(N-benzyloxyamino-2(R)-isobutyl-3-(N-benzyl-N-methylamino)methylsuccinyl]-L-phenylglycine-N-methylamide [an optically active isomer in which $R^2$ is hydrogen atom, $R^3$ is methyl and $R^5$ is N-benzyl-N-methylaminomethyl in the formula (IIb)]

(1) [4-benzyloxy-2(R)-isobutyl-3-methylenesuccinyl]-L-phenylglycine-N-methylamide [an optically active isomer in which $R^2$ is hydrogen and $R^3$ is methyl in the formula (XI)]:

3.0 g of [4-hydroxy-2(R)-isobutyl-3-methylenesuccinyl]-L-phenylglycine-N-methylamide obtained in Reference example 3 (4) was dissolved in 50 ml of DMF, and to this solution were added 1.5 g of sodium bicarbonate and 7.7 g of benzylbromide and the mixture was stirred for 21 hours at room temperature. To the reaction mixture was added 100 ml of water and the mixture was extracted with ethyl acetate, dried over anhydrous magnesium sulfate and concentrated in vacuo. Isolation and purification of the thus obtained residue by silica gel medium-pressure liquid chromatography (n-hexane/ethyl acetate=2/1) gave 2.8 g of [4-benzyloxy-2 (R)-isobutyl-3-methylenesuccinyl]-L-phenylglycine-N-methylamide.

$^1$H-NMR (DMSO-d$_6$) δ: 0.81 (3H, d, J=6.4 Hz), 0.83 (3H, d, J=6.4 Hz), 1.3–1.6 (2H, m), 1.6–1.7 (1H, m), 2.57 (3H, d, J=4.6 Hz), 3.7–3.8 (1H, m), 5.1–5.2 (2H, m), 5.38 (1H, d, J=7.8 Hz), 5.65 (1H, s), 6.17 (1H, s), 7.2–7.4 (10H, m), 8.19 (1H, d, J=4.6 Hz), 8.51 (1H, d, J=7.8 Hz)

(2) [4-benzyloxy-2(R)-isobutyl-3-(N-benzyl-N-methylaminomethyl)succinyl]-L-phenylglycine-N-methylamide [an optically active isomer in which R$^2$ is hydrogen atom, R$^3$ is methyl and R$^6$ is N-benzyl-N-methylaminomethyl in the formula (XII)]:

1.0 g of the compound obtained in (1) above and 0.32 g of N-benzylmethylamine were stirred together for 2 hours at 60° C. The thus obtained mixture of diastereomers (ratio 5:1) was purified by TLC, yielding 0.4 g of [4-benzyloxy-2(R)-isobutyl-3-(N-benzyl-N-methylaminomethyl) succinyl]-Lphenylglycine-N-methylamide as a single, optically active isomer.

$^1$H-NMR (CDCl$_3$) δ: 0.8 (3H, d, J=6.5 Hz), 0.85 (3H, d, J=6.5 Hz), 1.0–1.6 (3H,m), 2.1 (3H,s), 2.1–2.4 (2H,m), 2.8 (3H, s), 5.3 (1H, s), 5.8 (2H, s), 7.2–7.8 (15H, m) (3) [4-(N-benzyloxyamino)-2(R)-isobutyl-3-(N-benzyl-N-methylaminomethyl)succinyl]-L-phenylglycine-N-methylamide [an optically active isomer in which R$^2$ is hydrogen atom, R$^3$ is methyl and R$^5$ is N-benzyl-N-methylaminomethyl in the formula (IIb)]:

0.4 of the optically active isomer obtained in (2) above was dissolved in 30 ml of methanol and, after the addition of 100 mg of 10% Pd/C, catalytic reduction was carried out under hydrogen atmosphere. The catalyst was then removed by filtration and the solid obtained by concentration in vacuo was subjected to a reaction similar to that in Reference example 3 (6), yielding 0.12 g of the optically active compound, [4-(N-benzyloxyamino)-2(R)-isobutyl-3-(N-benzyl-N-methylamino)methylsuccinyl]-L-phenylglycine-N-methylamide.

1H-NMR (CDCl$_3$) δ: 0.8 (3H, d, J=6.5 Hz), 0.85 (3H, d, J=6.5 Hz), 1.0–1.6 (3H, m), 2.1 (3H, s), 2.1–2.3 (2H, m), 2.75 (3H, s), 2.7–3.5 (2H, m), 4.1 (2H, s), 4.85 (2H, s), 5.5 (1H, s), 7.3–7.5 (15H, m).

Reference Example 6

Preparation of [4-(N-benzyloxyamino)-2(R)-isobutylsuccinyl]-L-phenylglycine-N-ethylamide [an optically active isomer in which R$^2$ is hydrogen atom and R$^3$ is ethyl in the formula (IIa)]

(1) N-benzyloxycarbonyl-L-phenylglycine-N-ethylamide

Following the same reaction procedure as Reference example 1 (2) except that ethylamine solution in methanol was used instead of methylamine solution in methanol, N-benzyloxycarbonyl-L-phenylglycine-N-ethylamide was obtained from N-benzyloxycarbonyl-L-phenylglycine.

$^1$H-NMR (DMSO-d$_6$) δ: 1.03 (3H, t), 2.9–3.3 (2H, m), 5.03 (2H, s), 5.20 (1H, d), 7.2–7.6 (11H, m), 8.0–8.3 (1H)
(2) [4-(N-benzyloxyamino)-2(R)-isobutylsuccinyl]-L-phenylglycine-N-ethylamide:

Following the same reaction procedure as Reference 1 (3) except that N-benzyloxycarbonyl-L-phenylglycine-N-ethylamide was used instead of N-benzyloxycarbonyl-L-phenylglycine-N-methylamide, [4-(N-benzyloxyamino)-2 (R)-isobutylsuccinyl]-L-phenylglycine-N-ethylamide was obtained.

$^1$H-NMR (DMSO-d$_6$) δ: 0.82 (3H, d, J=6.3 Hz), 0.88 (3H, d, J=6.3 Hz), 0.98 (3H, t, J=7.2 Hz), 0.95–1.17 (1H, m), 1.30–1.55 (2H, m), 1.98 (1H, dd, J=7.2 Hz, 14.3 Hz), 2.14 (1H, dd, J=7.4 Hz, 14.3 Hz), 2.85–2.98 (1H, m), 3.02–3.12 (2H, m), 4.67 (1H, d, J=11.1 Hz), 4.71 (1H, d, J=11.1 Hz), 5.41 (1H, d, J=8.1 Hz), 7.20–7.42 (10H, m), 8.14 (1H, t, J=5.4 Hz), 8.44 (1H, d, J=8.1 Hz), 10.97 (1H,s).

Reference Example 7

Preparation of [4-(N-benzyloxyamino)-2(R)-isobutylsuccinyl]-L-(p-fluorophenyl)glycine-N-methylamide [an optically active isomer in which R$^2$ is fluorine atom and R$^3$ is methyl in the formula (IIa)]

(1) N-benzyloxycarbonyl-L-(p-fluorophenyl)glycine-N-methylamide

A mixture of 220 mg of L-(p-fluorophenyl)glycine, which was prepared by the method described in a literature [Bull. Chem. Soc. Jpn., 65, 2359–2365 (1992)], 20 ml of water and 551 mg of sodium carbonate was reacted with 244 mg of benzyloxycarbonyl chloride in dioxane under ice-cooling, washed with ethyl acetate, the aqueous solution acidified with hydrochloric acid, extracted with chloroform and dried over magnesium sulfate. Evaporation of the solvent in vacuo gave as an oily residue 400 mg of a N-benzyloxycarbony 1 compound. This was reacted with N-methylamine in a similar manner to Reference example 1 (2), yielding 262 mg of N-benzyloxycarbonyl-L-(p-fluorophenyl)glycine-N-methylamide.

$^1$H-NMR (CDCl$_3$) δ: 2.8 (3H, d), 5.05 (2H, s), 5.11 (1H, d), 5.6–5.8 (1H, m), 6.0–6.2 (1H, m), 6.8–7.5 (9H, m).
(2) [4-(N-benzyloxyamino)-2(R)-isobutylsuccinyl]-L-(p-fluorophenyl)glycine-N-methylamide:

Following the same reaction procedure as Reference 1 (3) except that N-benzyloxycarbonyl-L-(p-fluorophenyl) glycine-N-methylamide was used instead of N-benzyloxycarbonyl-L-phenylglycine-N-methylamide, [4-(N-benzyloxyamino)-2(R)-isobutylsuccinyl]-L-(p-fluorophenyl)glycine-N-methylamide was obtained.

$^1$H-NMR (DMSO-d$_6$) δ: 0.81 (3H, d, J=6.3 Hz), 0.85 (3H, d, J=6.3 Hz), 1.0–1.1 (1H, m), 1.35–1.52 (2H, m), 1.96 (1H, dd,J=7.0 Hz, 14.5 Hz), 2.12 (1H, dd, J=7.5 Hz, 14.5 Hz), 2.57 (3H, d, J=4.6 Hz), 2.8–2.9 (1H, m), 4.65 (1H, d, J=12 Hz), 4.69 (1H, d, J=12 Hz), 5.38 (1H, d, J=7.8 Hz), 7.11 (2H, dd, J=8.9 Hz, 8.9 Hz), 7.35 (5H, s), 7.40–7.45 (2H, m), 8.13 (1H, q, J=4.6 Hz), 8.47 (1H, d, J=7.8 Hz), 10.95 (1H, s).

Reference Example 8

Preparation of [4-(N-benzyloxyamino)-2(R)-isobutylsuccinyl]-L-(p-isopropylphenyl)glycine-N-methylamide [an optically active isomer in which R$^2$ is isopropyl and R$^3$ is methyl in the formula (IIa)]

(1) N-benzyloxycarbonyl-L-(p-isopropylphenyl)glycine-N-methylamide:

L-(p-isopropylphenyl)glycine, which was prepared by the method described in a literature [Bull. Chem. Soc. Jpn., 65, 2359–2365 (1992)] was N-benzyloxycarbonylated in a similar manner to that described in Reference example 7 (1), then reacted with methylamine in a similar manner to Reference example 1 (2), yielding N-benzyloxycarbonyl-L-(p-isopropylphenyl)glycine-N-methylamide.

$^1$H-NMR (CDCl$_3$) δ: 1.2 (6H, d), 2.75 (3H, d), 5.0 (2H, s), 5.18 (1H, d), 5.4–5.6 (1H, m), 5.9–6.1 (1H), 7.1–7.3 (9H,s)
(2) [4-(N-benzyloxyamino)-2(R)-isobutylsuccinyl]-L-(p-isopropylphenyl)glycine-N-methylamide:

Following the same reaction procedure as Reference example 1 (3) except that N-benzyloxycarbonyl-L-(p- isopropylphenyl)glycine-N-methylamide was used instead of N-benzyloxycarbonyl-L-phenylglycine-N-methylamide, [4-(N-benzyloxyamino)-2(R)-isobutylsuccinyl]-L-(p-isopropylphenyl)glycine-N-methylamide was obtained.

$^1$H-NMR (DMSO-d$_6$) δ: 0.82 (3H, d, J=6.3 Hz), 0.87 (3H, d, J=6.3 Hz), 1.0–1.2 (1H,m), 1.2 (3H, d, J=6.9 Hz), 1.35–1.52 (2H, m), 1.97 (1H, dd, J=6.8 Hz, 14.5 Hz), 2.12 (1H, dd, J=7.6 Hz, 14.5 Hz), 2.57 (3H, d,J=4.6 Hz), 2.75–2.92 (2H, m), 4.65 (1H, d, J=11 Hz), 4.69 (1H, d, J=11 Hz), 5.33 (1H, d,J=7.8 Hz), 7.13 (2H, d, J=8.1 Hz), 7.29 (2H, d, J=8.1 Hz), 7.35 (5H,s), 8.06 (1H, q, J=4.6 Hz), 8.37 (1H, d, J=7.8 Hz), 10.96 (1H, s)

Reference Example 9

Preparation of [4-(N-benzyloxyamino)-2(R)-isobutyl-3-methylsuccinyl]-L-phenylglycine-N-methylamide [an optically active isomer in which R$^2$ is hydrogen atom, R$^3$ is methyl and R$^5$ is methyl in the formula (IIb)]

(1) [4-hydroxy-2(R)-isobutyl-3-(RS)-methylsuccinyl]-L-phenylglycine-N-methylamide:

To 11.1 g of [4-hydroxy-2(R)-isobutyl-3-methylenesuccinyl]-L-phenylglycine-N-methylamide obtained in Reference example 3 (4) dissolved in 700 ml of ethanol was added 1.0 g of 10% Pd/C, and the mixture was stirred for 2 hours under hydrogen atmosphere. The catalyst was removed by filtration and the filtrate concentrated to dryness in vacuo, yielding 11 g of [4-hydroxy-2(R)-isobutyl-3-(RS)-methylsuccinyl]-L-phenylglycine-N-methylamide (a mixture of two diastereomers derived from the chiral carbon in position 3). This solid was found to be a mixture of two stereoisomers (diastereomer "e'" and "f'", respectively) having a retention time of about 8.1 minutes and about 9.5 minutes, respectively, in the following HPLC analysis.

HPLC conditions: column: Inertsil Prep-ODS (6×250 mm), GL Science,

Mobile phase: 0.1% TFA aqueous/acetonitril=6:4

Flow rate: 1 ml/min

A minute amount of the diastereomeric mixture was separated for analytic purpose by HPLC. The diastereomers exhibited the following spectrum, respectively.

Diastereomer "e'"

$^1$H-NMR (DMSO-d$_6$) δ: 0.8 (3H, J=6.5 Hz), 0.87 (6H, d, J=6.6 Hz), 0.9–1.1 (1H, m), 1.3–1.6 (2H, m), 2.2–2.4 (1H, m), 2.57 (3H, d, J=4.6 Hz), 2.6–2.8 (1H, m), 5.47 (1H,d,J= 8.0 Hz), 7.2–7.45 (5H, m), 8.12 (1H, d, J=4.6 Hz), 8.73 (1H, d, J=8.0 Hz), 12.16 (1H,bs)

Diastereomer "f'"

$^1$H-NMR (DMSO-d$_6$) δ: 0.82 (3H, d, J=6.5 Hz), 0.86 (3H,d, J=6.4 Hz), 0.95 (3H, d, J=7.1 Hz), 1.0–1.15 (1H, m), 1.45–1.6 (2H, m), 2.57 (3H, d, J=4.6 Hz), 2.5–2.6 (1H, m), 2.7–2.85 (1H, m), 5.39 (1H, d, J=7.8 Hz), 7.2–7.4 (5H, m), 8.12 (1H, d, J=4.6 Hz), 8.50 (1H, d, J=7.8 Hz), 12.18 (1H, bs)

(2) [4-(N-benzyloxyamino)-2(R)-isobutyl-3-methylsuccinyl]-L-phenylglycine-N-methylamide To a solution of 11 g of the compound obtained in (1) above dissolved in a mixture 150 ml of DMF and 200 ml of methylene chloride were added, under ice-cooling, 8.0 g of O-benzylhydroxylamine hydrochloride, 5.5 g of hydroxy-benzotriazol and 5.1 g of triethylamine and then 7.8 g of WSC, and the mixture was stirred overnight at room temperature. The solid precipitated during the reaction was collected by filtration and washed with dilute hydrochloric acid and then with a small amount of methanol, yielding 7.7 g of one of the optical isomers of [4-(N-benzyloxyamino)-2(R)-isobutyl-3-methylsuccinyl]-L-phenylglycine-N-methylamide.

While two stereoisomers (referred to as diastereomer "e" and "f", respectively) were observed in the reaction mixture which have a retention time of 8.2 minutes and 9.6 minutes, respectively, in the HPLC analysis below, the compound obtained following the above-described procedure was one of them, i.e., diastereomer "e".

HPLC conditions: column: Inertsil Prep-ODS (6×250 mm), GL Science,

Mobile phase: 0.1% TFA aqueous/acetonitril=5:5

Flow rate: 1 ml/min

Melting point: 256°–257° C. (dec.)

1H-NMR(DMSO-d$_6$) δ: 0.76 (3H, d, J=2.1 Hz), 0.78 (3H,d, J=2.5 Hz), 0.84 (3H, d, J=6.4 Hz), 0.9 (1H, m), 1.3 (2H, m), 2.1 (1H, m), 2.56 (3H, d, J=4.5 Hz), 2.66 (1H, m), 4.77 (2H, s), 5.46 (1H, d, J=8.0 Hz), 7.23–7.42 (10H, m), 8.07 (1H, dd, J=4.6 Hz), 8.74 (1H, d, J=8.0 Hz), 11.04(1H, s)

Elementary analysis (for C$_{25}$H$_{33}$N$_3$O$_4$): Calcd. (%) C, 68.31; H, 7.57; N, 9.56 Found (%) C, 68.08; H, 7.49; N, 9.51

EXAMPLE 1

Preparation of [4-(N-hydroxyamino)-2(R)-isobutylsuccinyl]-L-phenylglycine-N-methylamide [an optical isomer in which R$^1$ and R$^2$ are both hydrogen atom and R$^3$ is methyl in the formula (I)]

To 7.3 g of [4-(N-benzyloxyamino)-2(R)-isobutylsuccinyl]-L-phenylglycine-N-methylamide dissolved in 300 ml of methanol was added 200 mg of 10% Pd/C and subjected to catalytic reduction under the hydrogen pressure of 3 kg/m$^2$.

After the removal of the catalyst by filtration and concentration in vacuo, the residue obtained was recrystallized from a mixed solvent of THF/methanol, yielding 4 g of the titled compound as colorless crystals (yield; 71.8%).

Melting point: 169°–170° C.

[α]$_D$=+97.4° (c=0.2, MeOH)

$^1$H-NMR (DMSO-d$_6$) δ: 0.81 (3H, d, J=6.3 Hz), 0.87 (3H, d, J=6.3 Hz), 1.0–1.15 (1H, m), 1.45–1.6 (2H, m), 1.97 (1H, dd, J=7.4, 14.4 Hz), 2.13 (1H, dd, J=6.6, 14.4 Hz), 2.55 (3H, d, J=4.5 Hz), 2.8–2.95 (1H, m), 5.38 (1H, d, J=7.8 Hz), 7.2–7.4 (5H, m), 8.13 (1H, q, J=4.5 Hz), 8.45 (1H, d, J=7.8 Hz), 8.72 (1H, s), 10.36 (1H, s)

IR (KBr) cm$^{-1}$: 3296, 1644, 1538

Elementary analysis (for C$_{17}$H$_{25}$N$_3$O$_4$): Calcd. (%) C, 60.88; H, 7.51; N, 12.53 Found (%) C, 60.78; H, 7.63; N, 12.36

EXAMPLE 2

Preparation of [4-(N-hydroxyamino)-2(R)-isobutylsuccinyl]-L-(p-hydroxyphenyl)glycine-N-methylamide [an optically active isomer in which R$^1$ is hydrogen atom, R$^2$ is hydroxy and R$^3$ is methyl in the formula (I)]

To 0.54 g of [4-(N-benzyloxyamino)-2(R)-isobutylsuccinyl]-L-(p-hydroxyphenyl)glycine-N-methylamide obtained in Reference example 2 dissolved in 20 ml of methanol was added 50 mg of 10% Pd/C and catalytic reduction performed under normal hydrogen pressure. After the removal of the catalyst and concentration in vacuo, the residue obtained was purified by fractional HPLC, yielding 240 mg of the titled compound as colorless crystals (yield; 55.8%).

Melting point: 187°–188° C.

[α]$_D$=+116.6° (c=0.2, MeOH)

$^1$H-NMR (DMSO-d$_6$) δ: 0.80 (3H, d, J=6.3 Hz), 0.86 (3H, d, J=6.3 Hz), 1.0–1.15 (1H, m), 1.35–1.6 (2H, m), 1.95 (1H, dd, J=7.5, 14.4 Hz), 2.11 (1H, dd, J=6.8, 14.4 Hz), 2.55 (3H, d, J=4.5 Hz), 2.8–2.95 (1H, m), 5.22 (1H, d, J=7.7 Hz), 6.69

(2H, d, J=8.5 Hz), 7.16 (2H, d, J=8.5 Hz), 7.98 (1H, q, J=4.5 Hz), 8.29 (1H, d,J=7.7 Hz), 8.72 (1H,s), 9.37 (1H,s), 10.34 (1H,s)

IR (KBr) cm$^{-1}$: 3304, 3072, 1642, 1552, 1518, 1442

Elementary analysis (for $C_{17}H_{25}N_3O_5$): Calcd. (%) C, 58.11; H, 7.17; N, 11.96 Found (%) C, 57.88; H, 7.15; N, 11.93

EXAMPLE 3

Preparation of [4-(N-hydroxyamino)-2(R)-isobutyl-3-(morpholinomethyl)succinyl]-L-phenylglycine-N-methylamide [an optically active isomer in which $R^1$ is morpholinomethyl, $R^2$ is hydrogen atom and $R^3$ is methyl in the formula (I) (diastereomer "a")]

1.5 g of diastereomer "a'" of [4-(N-benzyloxyamino)-2(R)-isobutyl-3-(morpholinomethyl)succinyl]-L-phenylglycine-N-methylamide was dissolved in 20 ml of methanol and 20 ml of THF, subjected to catalytic reduction under hydrogen atmosphere. After the removal of the catalyst by filtration, the filtrate was concentrated in vacuo, yielding solid matter. This was crystallized from methanol/ether, giving 1.06 g of [4-(N-hydroxyamino)-2(R)-isobutyl-3-(morpholinomethyl)succinyl]-L-phenylglycine-N-methylamide as a single optically active isomer (referred to as diastereomer "a"), (yield; 85.8%).

Melting point: 216°–217° C. (dec.)

$[\alpha]_D$=+85.1° (c=0.2, MeOH)

$^1$H-NMR (DMSO-d$_6$) δ: 0.78 (3H, d, J=6.4 Hz), 0.83 (3H, d, J=6.4 Hz), 0.85–0.97 (1H, m), 1.35–1.46 (2H, m), 1.72 (1H, dd, J=3, 11.8 Hz), 1.90–1.92 (2H, m), 2.15–2.35 (3H, m), 2.56 (3H, d, J=4.6 Hz), 2.5–2.57 (2H, m), 3.4–3.45 (4H, m), 5.47 (1H, d, J=8 Hz), 7.2–7.45 (5H, m), 8.10 (1H, d,J=4.6 Hz), 8.66 (1H, d, J=8 Hz), 8.77 (1H, d, J=1.7 Hz), 10.36 (1H, d, J=1.7 Hz)

IR (KBr) cm$^{-1}$: 3312, 1646, 1566

Elementary analysis (for $C_{22}H_{34}N_4O_5 \cdot H_2O$) Calcd. (%) C, 58.39; H, 8.02; N, 12.38 Found (%) C, 58.43; H, 7.98; N, 12.39

EXAMPLE 4

Preparation of [4-(N-hydroxyamino)-2(R)-isobutyl-3-(morpholinomethyl)succinyl]-L-phenylglycine-N-methylamide.hydrochloride [the hydrochloride of an optically active isomer (diastereomer "a") in which $R^1$ is morpholinomethyl, $R^2$ is hydrogen atom and $R^3$ is methyl in the formula (I)]

To 0.2 g of [4-(N-hydroxyamino)-2(R)-isobutyl-3-(morpholinomethyl)succinyl]-L-phenylglycine-N-methylamide (diastereomer "a") obtained in Example 3 dissolved in 5 ml of methanol was added, under ice-cooling, 1 ml of 4N HCl/dioxane solution and the mixture was concentrated in vacuo, yielding 0.2 g of the titled hydrochloride as colorless crystals (yield; 92%).

Melting point: 150°–160° C. (dec.)

$[\alpha]_D$=+88.4° (c=0.2, MeOH)

$^1$H-NMR(DMSO-d$_6$) δ: 0.81 (3H, d, J=6.4 Hz), 0.85 (3H, d, J=6.4 Hz), 0.95–1.1 (1H, m), 1.4–1.55 (2H, m), 2.57 (3H, d, J=4.6 Hz), 2.6–3.2 (7H, m), 3.5–3.9 (5H, m), 5.43 (1H, d, J= 7.7 Hz), 7.2–7.5 (5H, m), 8.20 (1H, q, J=4.6 Hz), 8.92 (1H, d, J=7.7 Hz), 10.37 (1H, s), 10.84 (1H, s)

IR (KBr) cm$^{-1}$: 3270, 1648, 1530.

Elementary analysis (for $C_{22}H_{34}N_4O_5 \cdot H_2O \cdot HCl$) Calcd. (%) C, 54.04; H, 7.63; N, 11.46 Found (%) C, 53.76; H, 7.44; N, 11.34

EXAMPLE 5

Preparation of [4-(N-hydroxyamino)-2(R)-isobutyl-3-methylsuccinyl]-L-phenylglycine-N-methylamide [an optical isomer in which $R^1$ and $R^3$ are both methyl and $R^2$ is hydrogen atom in the formula (I) (diastereomer "c")]

To 125 mg of the crystals of [4-(N-benzyloxyamino)-2(R)-isobutyl-3-methylenesuccinyl]-L-phenylglycine-N-methylamide obtained in Reference example 4 dissolved in 5 ml of methanol was added 50 mg of 10% Pd/C and subjected to catalytic reduction. Removal of the catalyst and concentration in vacuo gave [4-(N-hydroxyamino)-2(R)-isobutyl-3-methylsuccinyl]-L-phenylglycine-N-methylamide as a mixture of two stereoisomers (production ratio was 3:1, referred to as diastereomer "c" and "d", respectively). Purification of this by fractional HPLC under the following condition gave 32 mg of diastereomer "c" (yield; 36%).

HPLC conditions: column: Inertsil Prep-ODS (20.0×250 mm), GL Science,

Mobile phase: 0.1% TFA aqueous/acetonitril=7:3

Flow rate: 10 ml/min

Retention time: diastereomer "c" approx. 9 min diastereomer "d" approx. 11 min (Physical properties of diastereomer "c")

Melting point: 224°–226° C.

$[\alpha]_D$=+129.6° (c=0.1, MeOH)

1H-NMR (DMSO-d$_6$) δ: 0.78 (3H, d, J=6.8 Hz), 0.79 (3H, d, J=6.3 Hz), 0.85 (3H, d, J=6.4 Hz), 0.9–0.95 (1H, m), 1.35–1.5 (2H, m), 2.10 (1H, m), 2.57 (3H, d, J=4.6 Hz), 2.6–2.7 (1H, m), 5.47 (1H, d, J=8 Hz), 7.2–7.4 (5H, m), 8.07 (1H, d, J=4.6 Hz), 8.72 (1H, d, J=8 Hz), 10.42 (1H, s)

Elementary analysis (for $C_{18}H_{27}N_3O_4 \cdot \frac{1}{4} H_2O$) Calcd. (%) C, 61.08; H, 7.97; N, 11.87 Found (%) C, 61.06; H, 7.92; N, 11.87

EXAMPLE 6

Preparation of [4-(N-hydroxyamino)-2(R)-isobutyl-3-(methylaminomethyl)succinyl]-L-phenylglycine-N-methylamide [an optical isomer in which $R^1$ is methylaminomethyl, $R^2$ is hydrogen atom and $R^3$ is methyl in the formula (I)]

110 mg of the optical isomer of [4-(N-benzyloxyamino)-2(R)-isobutyl-3-(N-benzyl-N-methylamino)methylsuccinyl]-L-phenylglycine-N-methylamide obtained in Reference example 5 was subjected, in methanol, to catalytic reduction in a similar manner to Example 5, yielding 50 mg of an optically active isomer of [4-(N-hydroxyamino)-2(R)-isobutyl-3-(N-methylaminomethyl)succinyl]-L-phenylglycine-N-methylamide.

Melting point: 177°–180° C.

$[\alpha]_D$=+93.4° (c=0.1, MeOH)

$^1$H-NMR (DMSO-d$_6$) δ: 0.79 (3H, d, J=6.4 Hz), 0.84 (3H, d,J=6.4 Hz), 0.9–0.98(1H, m), 1.35–1.5 (2H, m), 2.08 (3H, s), 2.1–2.3 (2H, m), 2.57 (3H, d, J=4.5 Hz), 2.6–2.7 (1H, m), 5.46 (1H, d, J=8 Hz), 7.2–7.4 (5H, m), 8.12 (1H, d, J=4.5 Hz), 8.69 (1H, d, J=8.1 Hz)

EXAMPLE 7

Preparation of [4-(N-hydroxyamino)-2(R)-isobutylsuccinyl]-L-phenylglycine-N-ethylamide [an optically active isomer in which $R^1$ and $R^2$ are both hydrogen atom and $R^3$ is ethyl in the formula (I)]

150 mg of [4-(N-benzyloxyamino)-2(R)-isobutylsuccinyl]-L-phenylglycine-N-ethylamide obtained in Reference example 6 was subjected to catalytic reduction in a similar manner to Example 1, yielding 54 mg of [4-(N-hydroxyamino)-2(R)-isobutylsuccinyl]-L-phenylglycine-N-ethylamide as crystalline powder.

Melting point: 185°–190° C.

$[\alpha]_D$=+71° (c=0.5, MeOH)

$^1$H-NMR (DMSO-d$_6$) δ: 0.82 (3H, d, J=6.3 Hz), 0.87 (3H, d, J=6.3 Hz), 0.98 (3H, t, J=7.2 Hz), 1.04–1.16 (1H, m), 1.38–1.55 (2H, m), 1.97 (1H, dd, J=7.5 Hz, 14.4 Hz), 2.13 (1H, dd, J=6.9 Hz, 14.4 Hz), 2.83–2.95 (1H, m), 3.02–3.12 (2H, m), 5.39 (1H, d, J=8 Hz), 7.22–7.42 (5H, m), 8.14 (1H, t, J=5.4 Hz), 8.43 (1H, d, J=8 Hz), 8.70 (1H, bs), 10.35 (1H, s)

Elementary analysis (for $C_{18}H_{27}N_3O_4$) Calcd. (%) C, 61.87; H, 7.79; N, 12.03 Found (%) C, 61.98; H, 7.85; N, 11.98

EXAMPLE 8

Preparation of [4-(N-hydroxyamino)-2(R)-isobutylsuccinyl]-L-(p-fluorophenyl)glycine-N-methylamide [an optically active isomer in which $R^1$ is hydrogen atom, $R^2$ is fluorine atom and $R^3$ is methyl in the formula (I)]

320 mg of [4-(N-benzyloxyamino)-2(R)-isobutylsuccinyl]-L-(p-fluorophenyl)glycine-N-methylamide obtained in Reference example 7 was subjected to catalytic reduction in a similar manner to Example 1, yielding 155 mg of [4-(N-hydroxyamino)-2(R)-isobutylsuccinyl]-L-(p-fluorophenyl)glycine-N-methylamide as crystalline powder.

Melting point: 170°–172° C.

$[\alpha]_D$=+78° (c=0.1, MeOH)

$^1$H-NMR (DMSO-$d_6$) δ: 0.81 (3H, d, J=6.3 Hz), 0.85 (3H, d, J=6.3 Hz), 1.0–1.1 (1H, m), 1.40–1.52 (2H, m), 1.96 (1H, dd, J=7.3 Hz, 14.4 Hz), 2.12 (1H, dd, J=7.0 Hz, 14.4 Hz), 2.6 (3H, d, J=4.6 Hz), 2.8–2.9 (1H, m), 5.36 (1H, d, J=7.8 Hz), 7.14 (2H, dd, J=8.9, 8.9 Hz), 7.4–7.45 (2H,m), 8.13 (1H, d, J=4.6 Hz), 8.45 (1H, d, J=7.8 Hz), 10.34 (1H,s)

IR (KBr) cm$^{-1}$: 3288, 2962, 1641, 1543, 1511

Elementary analysis (for $C_{17}H_{24}FN_3O_4$) Calcd. (%) C, 57.78; H, 6.85; N, 11.89 Found (%) C, 57.83; H, 6.96; N, 11.84

EXAMPLE 9

Preparation of [4-(N-hydroxyamino)-2(R)-isobutylsuccinyl]-L-(p-isopropylphenyl)glycine-N-methylamide [an optically active isomer in which $R^1$ is hydrogen atom, $R^2$ is isopropyl and $R^3$ is methyl in the formula (I)]

300 mg of [4-(N-benzyloxyamino)-2(R)-isobutylsuccinyl]-L-(p-isopropylphenyl)glycine-N-methylamide obtained in Reference example 8 was subjected to catalytic reduction in a similar manner to Example 1, yielding 180 mg of [4-(N-hydroxyamino)-2(R)-isobutylsuccinyl]-L-(p-isopropylphenyl)glycine-N-methylamide as crystalline powder.

Melting point: 219°–222° C.

$[\alpha]_D$=+95.3° (c=0.1, MeOH)

$^1$H-NMR (DMSO-$d_6$) δ: 0.80 (3H, d, J=6.3 Hz), 0.85 (3H, d, J=6.3 Hz), 1.0–1.08 (1H, m), 1.2 (6H, d, J=6.9 Hz), 1.47–1.52 (2H, m), 1.95 (1H, dd, J=7.5 Hz, 14.4 Hz), 2.15 (1H, dd, J=6.9 Hz, 14.4 Hz), 2.60 (2H, d, J=4.6 Hz), 2.80–2.92 (2H, m), 5.3 (1H, d, J=7.8 Hz), 7.2 (2H, d, J=8.2 Hz), 7.3 (2H, d,J=8.2 Hz), 8.05 (1H, d, J=4.6 Hz), 8.4 (1H, d, J=7.8 Hz), 8.7 (1H,d, J=1.6 Hz), 10.34 (1H, d, J=1.6 Hz)

IR (KBr) cm$^{-1}$: 3298, 2962, 1662, 1639, 1608, 1572

Elementary analysis (for $C_{20}H_{31}N_3O_4$) Calcd. (%) C, 63.64; H, 8.28; N, 11.13 Found (%) C, 63.47; H, 8.30; N, 11.13

EXAMPLE 10

Preparation of [4-(hydroxyamino)-2(R)-isobutyl-3-methylsuccinyl]-L-phenylglycine-N-methylamide [an optically active isomer in which $R^5$ and $R^3$ are both methyl and $R^2$ is hydrogen atom in the formula (I) (diastereomer "c")]

7.7 g of [4-(N-benzyloxyamino)-2(R)-isobutyl-3-methylsuccinyl]-L-phenylglycine-N-methylamide (diastereomer "e") obtained in Reference example 9 was suspended in 500 ml of DMF. To this was added 0.7 g of 10% Pd/C and the mixture stirred for 4 hours under hydrogen atmosphere. After the removal of the catalyst by filtration and concentration in vacuo, the residue was recrystallized from methanol, yielding 5.2 g of the titled compound.

In HPLC analysis, this compound was eluted with the same retention time as diastereomer "c" prepared in Example 5, and its $^1$H-NMR spectrum was identical with that of diastereomer "c".

Melting point: 217°–219° C.

$[\alpha]_D$=+136° (c=0.1, MeOH)

Elementary analysis (for $C_{18}H_{27}N_3O_4$) Calcd. (%) C, 61.87; H, 7.79; N, 12.03 Found (%) C, 61.70; H, 7.79; N, 11.97

EXAMPLE 11

Preparation of sodium salt of [4-(N-hydroxyamino)-2(R)-isobutyl-3-methyl-succinyl]-L-phenylglycine-N-methylamide [an optically active isomer (diastereomer "c") in which $R^1$ and $R^3$ are methyl and $R^2$ is hydrogen atom in the formula (I)]

To 101 mg of the optically active isomer (diastereomer "c") of [4-(N-hydroxyamino)-2(R)-isobutyl-3-methylsuccinyl-L-phenylglycine-N-methylamide dissolved in 20 ml of methanol was added, under ice-cooling, 2.9 ml of ¹⁄₁₀N sodium hydroxide aqueous solution and the mixture stirred for 5 minutes. The resulted solution was concentrated to dryness in vacuo, yielding 107 mg of [4-(N-hydroxyamino)-2(R)-isobutyl-3-methylsuccinyl]-L-phenylglycine-N-methylamide sodium salt.

$^1$H-NMR (DMSO-$d_6$) δ: 0.75 (3H, d, J=6.6 Hz), 0.77 (3H, d, J=5.4 Hz), 0.82 (3H, d, J=6.3 Hz), 1.0 (1H, m), 1.4 (2H,m), 2.0 (1H, m), 2.4–2.6 (1H, m), 2.56 (3H, d, J=4 Hz), 5.42 (1H, d, J=7.9 Hz), 7.2–7.4 (5H, m), 8.02 (1H, d, J=4.3 Hz), 9.52 (1H, d, J=7.6 Hz)

EXAMPLE 12

Tablets are obtained as follows containing 100 mg/tablet of [4-(hydroxyamino)-2(R)-isobutyl-3-methylsuccinyl]-L-phenylglycine-N-methylamide (the compound of Example 5).

| Components | Amount |
| --- | --- |
| Active principle (the compound of Example 5) | 100 parts by weight |
| Cornstarch | 46 parts by weight |
| Microcrystalline cellulose | 93 parts by weight |
| hydroxypropylcellulose | 2 parts by weight |
| Magnesium stearate | 4 parts by weight |

[Procedure]

The active principle, cornstarch and microcrystalline cellulose are admixed and to this mixture is added hydroxypropylcellulose dissolved in 50 parts by weight of water, followed by sufficient kneading. The paste is then passed through a sieve to granulate, dried, mixed with magnesium stearate and made into tables of 250 mg each.

EXAMPLE 13

Preparation of granules

Granules are obtained as follows containing 200 mg of [4-(hydroxyamino)-2(R)-isobutyl-3-methylsuccinyl]-L-phenylglycine-N-methylamide (the compound of Example 5).

[Formula]

| Components | Amount |
| --- | --- |
| Active principle (the compound of Example 5) | 200 parts by weight |
| Lactose | 185 parts by weight |
| Cornstarch | 109 parts by weight |
| hydroxypropylcellulose | 6 parts by weight |

[Procedure]

The active principle, lactose and cornstarch are admixed and to this is added hydroxypropylcellulose dissolved in 120 parts by weight of water, followed by sufficient kneading. The paste is passed through a 20-mesh sieve to granulate, dried and size adjusted to obtain granules.

EXAMPLE 14
Preparation of capsules

Capsules are obtained as follows containing 100 mg of [4-(hydroxyamino)-2(R)-isobutyl-3-methylsuccinyl]-L-phenylglycine-N-methylamide (the compound of Example 5) per capsule.

[Formula]

| Components | Amount |
| --- | --- |
| Active principle (the compound of Example 5) | 100 parts by weight |
| Lactose | 35 parts by weight |
| Cornstarch | 60 parts by weight |
| Magnesium stearate | 5 parts by weight |

[Procedure]

The above components are mixed together and 200 mg each of this mixed powder is encapsulated to obtain capsules.

We claim:

1. An acylphenylglycine compound of formula (I),

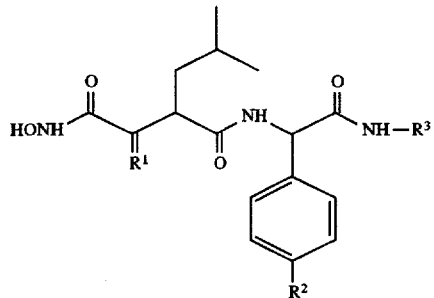

(I)

wherein $R^1$ is hydrogen, methyl, methylaminomethyl or morpholinomethyl; $R^2$ is hydrogen, hydroxy, fluorine, or $C_1$–$C_4$ linear or branched chain alkyl; and $R^3$ is $C_1$–$C_4$ linear or branched chain alkyl, or a pharmaceutically acceptable salt thereof.

2. The acylphenylglycine compound or the pharmaceutically acceptable salt thereof according to claim 1 wherein $R^1$ and $R^3$ are both methyl and $R^2$ is hydrogen.

3. A method for the treatment of diseases caused by increased collagenase activity, comprising administering an agent which comprises as an active principle the acylphenylglycine derivative or the pharmaceutically acceptable salt thereof according to claim 1.

4. The method according to claim 3 wherein the diseases caused by increased collagenase activity are joint diseases or diseases due to bone resorption.

5. A method for the treatment of diseases caused by increased collagenase activity, comprising administering an agent which comprises as an active principle the acylphenylglycine derivative or the pharmaceutically acceptable salt thereof according to claim 2.

6. The acylphenylglycine compound or salt of claim 1, wherein $R^1$ and $R^2$ are hydrogen and $R^3$ is methyl.

7. A compound according to claim 1 which is [4-(N-hydroxyamino)-2(R)-isobutylsuccinyl]-L-phenylglycine-N-methylamide.

8. A compound according to claim 1 which is [4-(N-hydroxyamino)-2(R)-isobutyl-3-methylsuccinyl]-L-phenylglycine-N-methylamide.

9. A compound according to claim 1 which is:
[4-(N-hydroxyamino)-2(R)-isobutylsuccinyl]-L-(p-hydroxyphenyl)glycine-N-methylamide,
[4-(N-hydroxyamino)-2(R)-isobutyl-3-(morpholinomethyl)succinyl]-L-phenylglycine-N-methylamide hydrochloride,
[4-(N-hydroxyamino)-2(R)-isobutyl-3-(methylaminomethyl)succinyl]-L-phenylglycine-N-methylamide,
[4-(N-hydroxyamino)-2(R)-isobutylsuccinyl]-L-phenylglycine-N-ethylamide,
[4-(N-hydroxyamino)-2(R)-isobutylsuccinyl]-L-(p-fluorophenyl)glycine-N-methylamide, or
[4-(N-hydroxyamino)-2(R)-isobutylsuccinyl]-L-(p-isopropylphenyl)glycine-N-methylamide.

10. An agent for treatment of diseases caused by increased collagenase activity which agent comprises as an active principle the acylphenylglycine derivative or the pharmaceutically acceptable salt thereof according to claim 1.

11. A method according to claim 4, wherein the diseases are rheumatoid arthritis, osteoarthritis, hypercalcemia or osteoporosis.

12. An acylphenylglycine compound of formula (I),

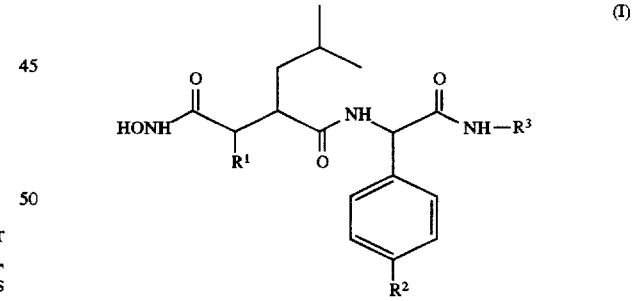

(I)

wherein $R^1$ is hydrogen, methyl, methylaminomethyl or morpholinomethyl; $R^2$ is hydrogen or hydroxy; and $R^3$ is $C_1$–$C_4$ linear or branched chain alkyl, or a pharmaceutically acceptable salt thereof.

* * * * *